(12) United States Patent
Choi

(10) Patent No.: US 11,096,673 B2
(45) Date of Patent: Aug. 24, 2021

(54) ULTRASOUND IMAGING SYSTEM WITH A TRANSMIT PULSE SEQUENCE GENERATOR CIRCUIT

(71) Applicant: MTEC GLOBAL CO., LTD., Changwon-si (KR)

(72) Inventor: Kyusun Choi, State College, PA (US)

(73) Assignee: MTEC GLOBAL CO., LTD., Changwon-si (KR)

( * ) Notice: Subject to any disclaimer, the term of this patent is extended or adjusted under 35 U.S.C. 154(b) by 0 days.

(21) Appl. No.: 16/908,141

(22) Filed: Jun. 22, 2020

(65) Prior Publication Data

US 2020/0315590 A1 Oct. 8, 2020

Related U.S. Application Data

(63) Continuation-in-part of application No. 16/446,110, filed on Jun. 19, 2019, now Pat. No. 10,687,782.

(60) Provisional application No. 62/686,709, filed on Jun. 19, 2018.

(51) Int. Cl.
| | |
|---|---|
| *A61B 8/00* | (2006.01) |
| *G16H 30/20* | (2018.01) |
| *H03K 23/50* | (2006.01) |
| *H03K 19/20* | (2006.01) |

(52) U.S. Cl.
CPC ............... *A61B 8/54* (2013.01); *G16H 30/20* (2018.01); *H03K 23/50* (2013.01); *H03K 19/20* (2013.01)

(58) Field of Classification Search
None
See application file for complete search history.

(56) References Cited

U.S. PATENT DOCUMENTS

| | | | | |
|---|---|---|---|---|
| 3,509,484 A | * | 4/1970 | Basse ................... | H03B 21/025 331/44 |
| 3,548,319 A | * | 12/1970 | Price ..................... | H03K 23/50 377/106 |
| 9,812,216 B1 | | 11/2017 | Kantipudi | |
| 2003/0028832 A1 | | 2/2003 | Schaber et al. | |

(Continued)

FOREIGN PATENT DOCUMENTS

JP 2000139905 A 5/2000

OTHER PUBLICATIONS

Eliza Strickland, "New 'Ultrasound on a Chip' Tool Could Revolutionize Medical Imaging," IEEE Spectrum's biomedical engineering blog, Oct. 27, 2017.

(Continued)

*Primary Examiner* — Lincoln D Donovan
*Assistant Examiner* — Khareem E Almo
(74) *Attorney, Agent, or Firm* — Dinsmore & Shohl LLP

(57) ABSTRACT

A transmit signal generator is provided. The transmit signal generator has an n−1 bit comparator having a first set of n−1 input lines and a second set of n−1 input lines and an output line, the n−1 bit comparator operable to compare signals of the first set of n−1 input lines and signals of the second set of n−1 input lines and provide the output of the n−1 bit comparator based on the comparison, and an n-bit binary counter having a clock signal input line, a reset signal input line, a clock enable line connected to the output line of the n−1 bit comparator, and n output lines. One of the n output lines provides a sequence of pulse as an output of the transmit signal generator.

20 Claims, 16 Drawing Sheets

(56) References Cited

U.S. PATENT DOCUMENTS

| | | | |
|---|---|---|---|
| 2011/0060226 A1 | 3/2011 | Yen et al. | |
| 2012/0051493 A1* | 3/2012 | Gomm | H03L 7/085 |
| | | | 377/34 |
| 2013/0077445 A1 | 3/2013 | Um et al. | |
| 2015/0028190 A1* | 1/2015 | Shin | H04N 13/271 |
| | | | 250/208.1 |
| 2018/0350411 A1* | 12/2018 | Ware | G06F 1/12 |
| 2019/0201074 A1 | 7/2019 | Yates et al. | |
| 2019/0380675 A1 | 12/2019 | Choi | |
| 2020/0129152 A1* | 4/2020 | Jain | G01S 15/8915 |
| 2020/0315590 A1* | 10/2020 | Choi | A61B 8/54 |

OTHER PUBLICATIONS

Ira O. Wygant, et al., "Integration of 2D CMUT Arrays with Front-End Electronics for Volumetric Ultrasound Imaging," IEEE Transactions on Ultrasonics, Ferroelectronics, and Frequency Control, vol. 55, No. 2, pp. 327-342, Feb. 2008.

\* cited by examiner

1. Continuous pulse sequence

2. Single pulse sequence

3. Two pulse sequence

4. Four pulse sequence

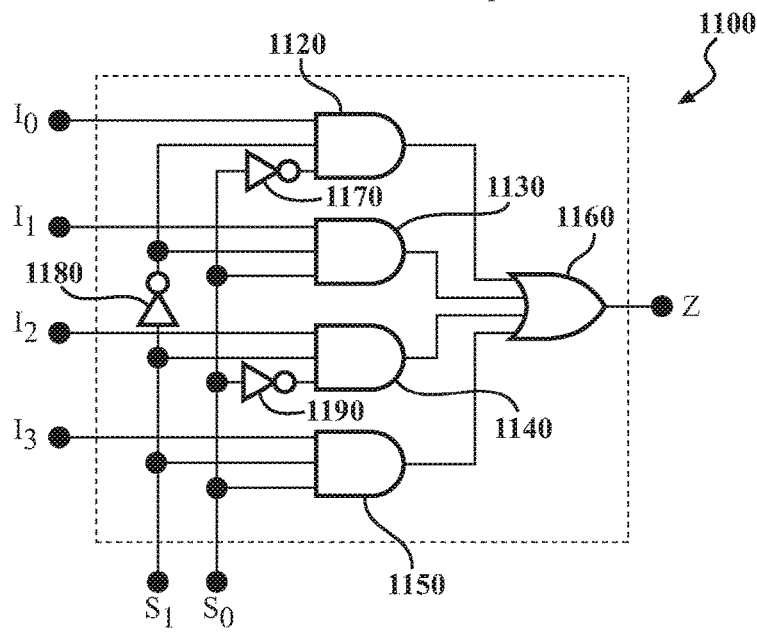
FIG. 11A  FIG. 11B
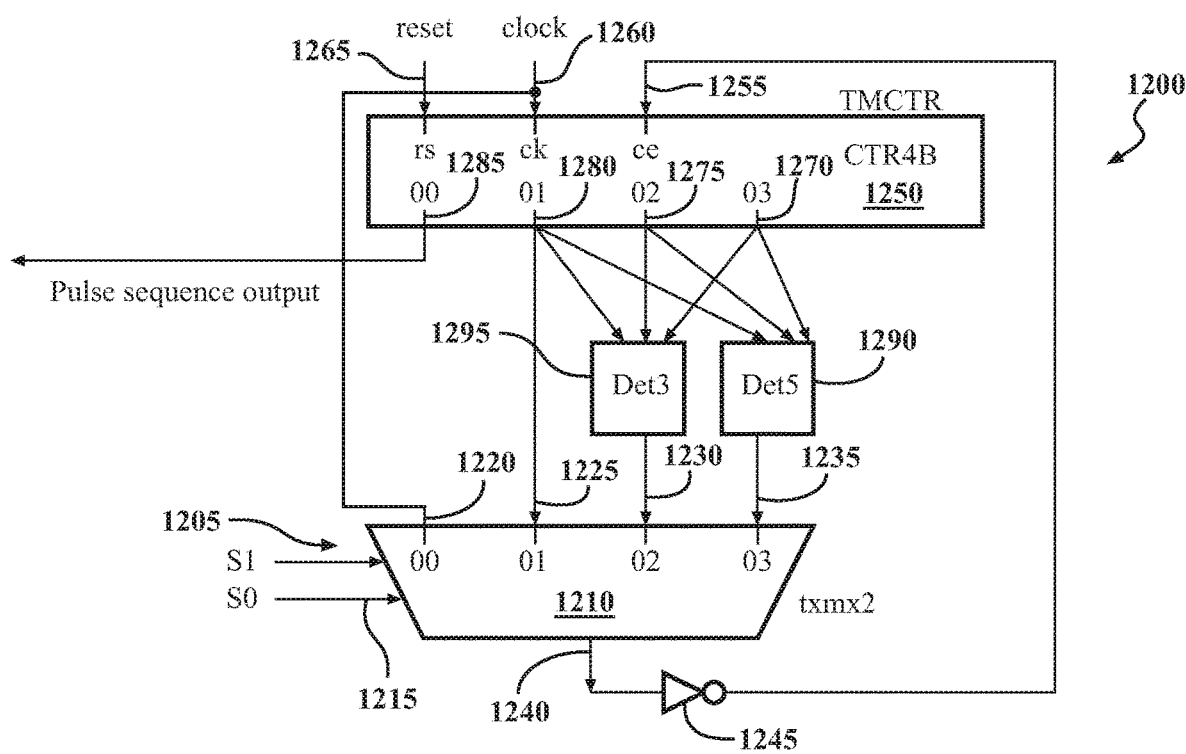
FIG. 12

(1) Detect 3 (Det3) circuit (2) Detect 5 (Det5) circuit

ULTRASOUND IMAGING SYSTEM WITH A TRANSMIT PULSE SEQUENCE GENERATOR CIRCUIT

REFERENCE TO RELATED APPLICATION

This application is a continuation-in-part of U.S. patent application Ser. No. 16/446,110 filed on Jun. 19, 2019 which claims the benefit of U.S. Provisional Patent Application Ser. No. 62/686,709, filed Jun. 19, 2018, the entire contents of both of which are incorporated herein by reference.

FIELD OF THE INVENTION

The present invention generally relates to the field of ultrasound imaging system with a transmit pulse sequence generator circuit.

BACKGROUND OF THE INVENTION

Ultrasound imaging (sonography) uses high-frequency sound waves to view inside the body. Because ultrasound images are captured in real-time, they can also show movement of the body's internal organs as well as blood flowing through the blood vessels. Unlike X-ray imaging, there is no ionizing radiation exposure associated with ultrasound imaging.

Ultrasound devices may be used to perform diagnostic imaging and/or treatment. Ultrasound imaging may be used to see internal soft tissue body structures. Ultrasound imaging may be used to find a source of a disease or to exclude any pathology. Ultrasound devices use sound waves with frequencies which are higher than those audible to humans.

Ultrasonic images are made by sending pulses of ultrasound into tissue using a probe. The sound waves are reflected off the tissue, with different tissues reflecting varying amounts of sound. These reflected sound waves may be recorded and displayed as an image to the operator. The strength (amplitude) of the sound signal and the time it takes for the wave to travel through the body provide information used to produce an image.

Many different types of images can be formed using ultrasound devices. The images can be real-time images. For example, images can be generated that show two-dimensional cross-sections of tissue, blood flow, motion of tissue over time, the location of blood, the presence of specific molecules, the stiffness of tissue, or the anatomy of a three-dimensional region.

In an ultrasound exam, a transducer (probe) is placed directly on the skin or inside a body opening. A thin layer of gel is applied to the skin so that the ultrasound waves are transmitted from the transducer through the gel into the body. The ultrasound image is produced based on the reflection of the waves off of the body structures. The strength (amplitude) of the sound signal and the time it takes for the wave to travel through the body provide the information necessary to produce an image.

Ultrasound imaging is a medical tool that can help a physician evaluate, diagnose and treat medical conditions. Common ultrasound imaging procedures include: Abdominal ultrasound (to visualize abdominal tissues and organs), Bone sonometry (to assess bone fragility), Breast ultrasound (to visualize breast tissue), Doppler fetal heart rate monitors (to listen to the fetal heart beat), Doppler ultrasound (to visualize blood flow through a blood vessel, organs, or other structures), Echocardiogram (to view the heart), Fetal ultrasound (to view the fetus in pregnancy), Ultrasound-guided biopsies (to collect a sample of tissue), Ophthalmic ultrasound (to visualize ocular structures, and Ultrasound-guided needle placement (in blood vessels or other tissues of interest).

Ultrasound imaging has been used for many years and has an excellent safety record. It is based on non-ionizing radiation, so it does not have the same risks as X-rays or other types of imaging systems that use ionizing radiation.

There are various ultrasound procedures that may be used to produce an ultrasound image. The choice of which type of procedure to use depends on the goals for a particular test, the phenomena being investigated and what equipment is available. The most common type of ultrasound picture is a series of flat, two-dimensional cross section images of the scanned tissue. Referred to simply as 2D ultrasound, this mode of scanning is still standard for many diagnostic and obstetric situations after a half-century of use.

In recent years, 2D ultrasound images have also been projected into three-dimensional representations. This is achieved by scanning tissue cross sections at many different angles and reconstructing the data received into a three-dimensional image. A common use for 3D ultrasound pictures is to provide a more complete and realistic image of a developing fetus. By updating 3D ultrasound images in rapid succession, sonographers can also create 4D ultrasound pictures. In the 4D ultrasound, the fourth dimension, time, adds movement and creates the most realistic representation of all.

In some cases, 3D and 4D ultrasound pictures may reveal abnormalities not readily seen using 2D ultrasound. Evaluating blood flow as it moves through blood vessels is a common component of many of the types of ultrasound. While traditional 2D ultrasound and its three-dimensional offshoot show internal tissues and structures, a different kind of ultrasound is required to evaluate blood flow and pressure within a blood vessel.

A Doppler ultrasound analysis bounces high-frequency sound waves off blood cells in motion and records changes in frequency of the sound waves as they echo back to the transducer probe. It then converts this data into a visual representation of how fast and in what direction blood is flowing. A useful diagnostic tool may be preferable in many cases to X-ray angiography because it does not require injecting the patient with contrasting dye.

Three types of Doppler ultrasound are currently in use in addition to routine grayscale imaging. Of these, color Doppler uses a wide choice of colors to visualize blood flow measurements and embed them within a conventional 2D ultrasound of tissues and structures. This provides a more pronounced representation of blood flow speed and direction than is the case with traditional grayscale images. Power Doppler provides color imaging of more sensitive and detailed blood flow measurements than regular color Doppler does. It can sometimes even achieve images in situations not accessible with color Doppler. However, power Doppler is limited in another way because it cannot indicate the direction in which blood is flowing. Like conventional and color Doppler, spectral Doppler can scan to determine both blood flow and direction but displays this data in graphic form rather than with grayscale or color images.

It is known to use a function generator for generating ultrasound frequency pulses. The basic function generator is usually a piece of electronic equipment or software used to generate different types of electrical waveforms over a wide range of frequencies. More advanced function generators, such as arbitrary waveform generators (AWG), use direct digital synthesis (DDS) techniques to generate any waveform that can be described by a table of amplitudes. Direct digital synthesis (DDS) is a method employed by frequency synthesizers used for creating arbitrary waveforms from a single, fixed-frequency reference clock. DDS is used in applications such as signal generation, local oscillators in communication systems, function generators, mixers, modulators, sound synthesizers and as part of a digital phase-locked loop.

The equipment and software currently required for generating a sequence of pulses have limitations of being complex and costly. Thus, it is desirable to provide a better solution in order to overcome limitations of the existing technologies.

SUMMARY OF THE INVENTION

In one embodiment, a transmit signal generator for generating a sequence of pulses is provided. The transmit signal generator includes an n−1 bit comparator having a first set of n−1 input lines and a second set of n−1 input lines and an output line providing an output of the n−1 bit comparator, the n−1 bit comparator operable to compare signals of the first set of n−1 input lines and signals of the second set of n−1 input lines and provide the output of the n−1 bit comparator based on the comparison, and an n-bit binary counter having a clock signal input line connected to a clock signal input, a reset signal input line connected to a reset signal input, a clock enable line connected to the output line of the n−1 bit comparator providing the output of the n−1 bit comparator as an input signal for the clock enable line, and n output lines, one of the n output lines providing a sequence of pulse as an output of the transmit signal generator and the remaining of the n output lines of the n-bit binary counter each connected to one of the second set of n−1 input lines of the n−1 bit comparator. The output of the transmit signal generator provides a continuous pulse or an N pulse sequence as the output based on the signals of the second set of n−1 input lines and the reset signal input initiating generation of the sequence of pulses, wherein $N \leq 2^{n-1}-1$ and n is an integer.

In another embodiment, a transmit signal generator for generating a sequence of pulses is provided. The transmit signal generator includes a n-bit binary counter having a clock signal input line connected to a clock signal input, a reset signal input line connected to a reset signal input, a clock enable line, and n output lines. One of the n output lines provides a sequence of pulse as an output of the transmit signal generator, and the clock enable line is connected to one of the remaining of the n output lines of the n-bit binary counter. The output of the transmit signal generator provides a L pulse sequence as the output based on which one of the remaining of the n output lines of the n-bit binary counter is connected to the clock enable line, wherein L is $2^{m-2}$, $m \leq n$, and m and n are an integer.

In yet another embodiment, a transmit signal generator for generating a sequence of pulses is provided. The transmit signal generator includes a $2^n$-to-1 multiplexer having $2^n$ input lines, one of the $2^n$ input lines being connected to a clock signal input, n selector lines connected to a selector signal and an output line providing an output of the $2^n$-to-1 multiplexer, the $2^n$-to-1 multiplexer operable to select one of the $2^n$ input lines as the output of the $2^n$-to-1 multiplexer based on the selector signal, and a $2^n$-bit binary counter having a clock signal input line connected to the clock signal input, a reset signal input line connected to a reset signal input, a clock enable line connected to the output line of the $2^n$-to-1 multiplexer providing the output of the $2^n$-to-1 multiplexer as an input signal for the clock enable line, and $2^n$ output lines, one of the $2^n$ output lines providing a sequence of pulse as an output of the transmit signal generator and the remaining $2^n$ output lines of the $2^n$-bit binary counter each connected to one of the remaining $2^n$ input lines of the $2^n$-to-1 multiplexer. The output of the transmit signal generator provides a continuous pulse or an N pulse sequence as the output based on the selector signal and the reset signal input initiating generation of the sequence of pulses, wherein $N \leq 2^n$ and n is an integer.

These and additional features provided by the embodiments of the present disclosure will be more fully understood in view of the following detailed description, in conjunction with the drawings.

BRIEF DESCRIPTION OF THE DRAWINGS

The accompanying drawings, which are included to provide a further understanding of the invention and are incorporated in and constitute a part of this application, illustrate embodiment (s) of the invention and together with the description serve to explain the principle of the invention. In the drawings:

FIG. 11*a* is a detailed diagram of a digital 4-to-1 multiplexer circuit example;

FIG. 11*b* is a truth table for the circuit shown in FIG. 11*b*

FIG. 12 is a circuit diagram of another embodiment of the PSGC, for some odd number of pulse outputs;

DETAILED DESCRIPTION OF THE INVENTION

For simplicity and clarity, the Figures of the present disclosure illustrate a general manner of construction of various embodiments. Descriptions and details of well-known features and techniques may be omitted to avoid unnecessarily obscuring the discussion of described embodiments of the present disclosure. It should be understood that the elements of the Figures are not necessarily drawn to scale, and that the dimensions of some elements may be exaggerated relative to other elements for enhancing understanding of described embodiments.

The proposed technology is discussed herewith in detail in reference to the Figures. This disclosure describes various embodiments related to a ultrasound transmit (Tx) pulse sequence generator circuit (PSGC) that generates a pulse signal with a selectable number of pulses. This circuit is compact, flexible, low-power, comparable with digital technology, easily implementable on a FPGA (Field Programmable Gate Array) chip, and can be integrated into a semiconductor chip. The PSGC takes clock signal input, reset signal input, and pulse selector inputs (s0, s1, s2, etc.). It generates a pulse sequence output (tps).

Figure 1:
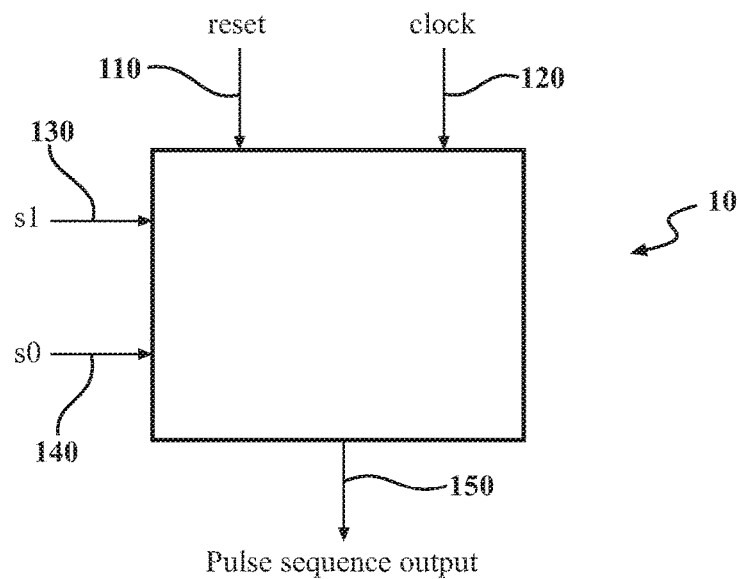
FIG. 1 is a block diagram of a pulse sequence generator circuit (PSGC)

As noted above, FIG. 1 is a block diagram of an embodiment of a pulse sequence generator circuit (PSGC) 10 according to this disclosure. Referring now to FIG. 1, the PSGC 10 takes an input clock signal 120, pulse selector inputs s1 (130) and s0 (140) and generates a pulse sequence output 150 depending on the reset signal 110. The PSGC 10 divides the input clock signal 120 by half and generates the pulse sequence output 150. For example, a 20 MHz pulse sequence output 150 is generated from a 40 MHz input clock signal and a 10 MHz pulse sequence output 150 is generated from a 20 MHz input clock signal. The reset signal 110 determines the starting of the pulse sequence output 150. In a non-limiting example, the reset signal 110 is initially active-high and when the reset signal 110 ends, the pulse sequence output 150 starts. In some embodiments, the reset signal 110 may initially be held active-low and when the reset signal 110 turns high, the pulse sequence output 150 starts.

The pulse selector inputs s1 (130) and s0 (140) determine the number of pulses present in the pulse sequence output 150. For example, the number of pulses in the pulse sequence output 150 that may be selected are 1, 2, 4, 8, etc. In one combination of the pulse selector inputs s1 (130) and s0 (140), the pulse sequence output 150 may be a continuous pulse.

Figure 2:
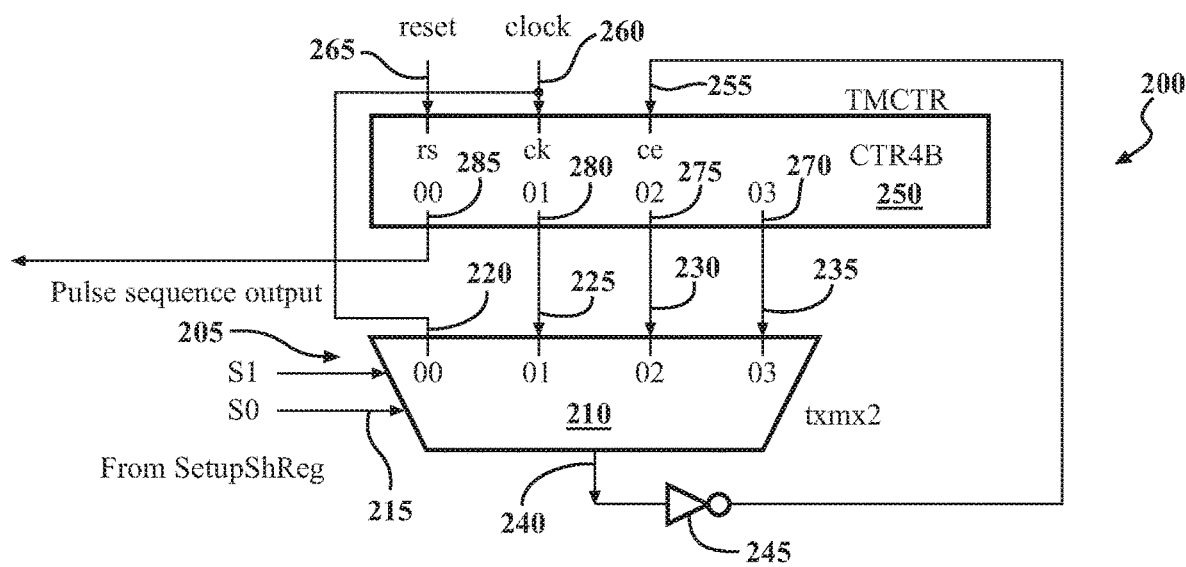
FIG. 2 shows an embodiment of a PSGC with four different pulse output sequences.

As noted above, FIG. 2 shows an embodiment of a PSGC with four outputs. Referring now to FIG. 2, the PSGC 200 consist of two functional circuit modules, i.e. a 4-to-1 multiplexer 210 and a 4-bit binary counter circuit 250. In FIG. 2, the 4-to-1 multiplexer 210 is labeled as "txmx2" and the 4-bit binary counter circuit 250 is labeled as "CTR4B". The multiplexer 210 takes input signals (220, 225, 230, 235) and pulse selector inputs (205/s1, 215/s0) and generates an output signal 240.

The input signal line 220 takes an input clock signal 260. The selection made by the multiplexer 210 between the input signals (220, 225, 230, 235) is determined by the pulse selector inputs (205/s1, 215/s0). Therefore, one of the input signals (220, 225, 230, 235) is selected and forwarded as the output signal 240 based on the pulse selector inputs (205/s1, 215/s0).

The counter circuit 250 takes clock enable signal "ce" 255, input clock signal 260, reset signal 265 and generates output signals 270, 275, 280 and 285. The output signal 285 provides a pulse sequence output for the PSGC 200. The remaining output signals 270, 275 and 280 respectively provide input signals 235, 230, 225 for the multiplexer 210. However, it should be understood that this is merely illustrative, and the other output signals may instead be used for providing the pulse sequence output. For example, in some embodiments of the PSGC 200, the output signals 270, 275 or 280 may provide the pulse sequence output. In that case, the remaining output signals would accordingly be connected to provide input signals for the multiplexer 210. As shown in FIG. 2, the output signal 240 of the multiplexer 210 is connected to the clock enable signal "ce" 255 through an inverter gate 245.

PSGC 200 uses a counter circuit 250 with clock enable signal "ce" as an active-high signal input. Therefore, the inverter gate 245 is required to connect the output signal 240 of the multiplexer 210 to the clock enable signal "ce" 255 through the inverter gate 245. However, it should be understood that this is merely illustrative, and other embodiments of PSGC 200 may not require the inverter gate 245. For example, a counter circuit 250 in an embodiment of PSGC 200 may present the clock enable signal "ce" as an active-low signal input, and therefore, would not require inverter gate 245.

In some embodiments, the PSGC 200 divides the input clock signal 260 by half and generates the output signal 285. For example, a 20 MHz output signal 285 is generated from a 40 MHz input clock signal 260 and a 10 MHz output signal 285 is generated from a 20 MHz input clock signal 260. The reset signal 265 determines the starting of the output signal 285. In a non-limiting example, the reset signal 265 is initially active-high and when the reset signal 265 ends, the output signal 285 starts. In some embodiments, the reset signal 265 may initially be held active-low and when the reset signal 265 turns high, the output signal 285 starts.

Figure 3:
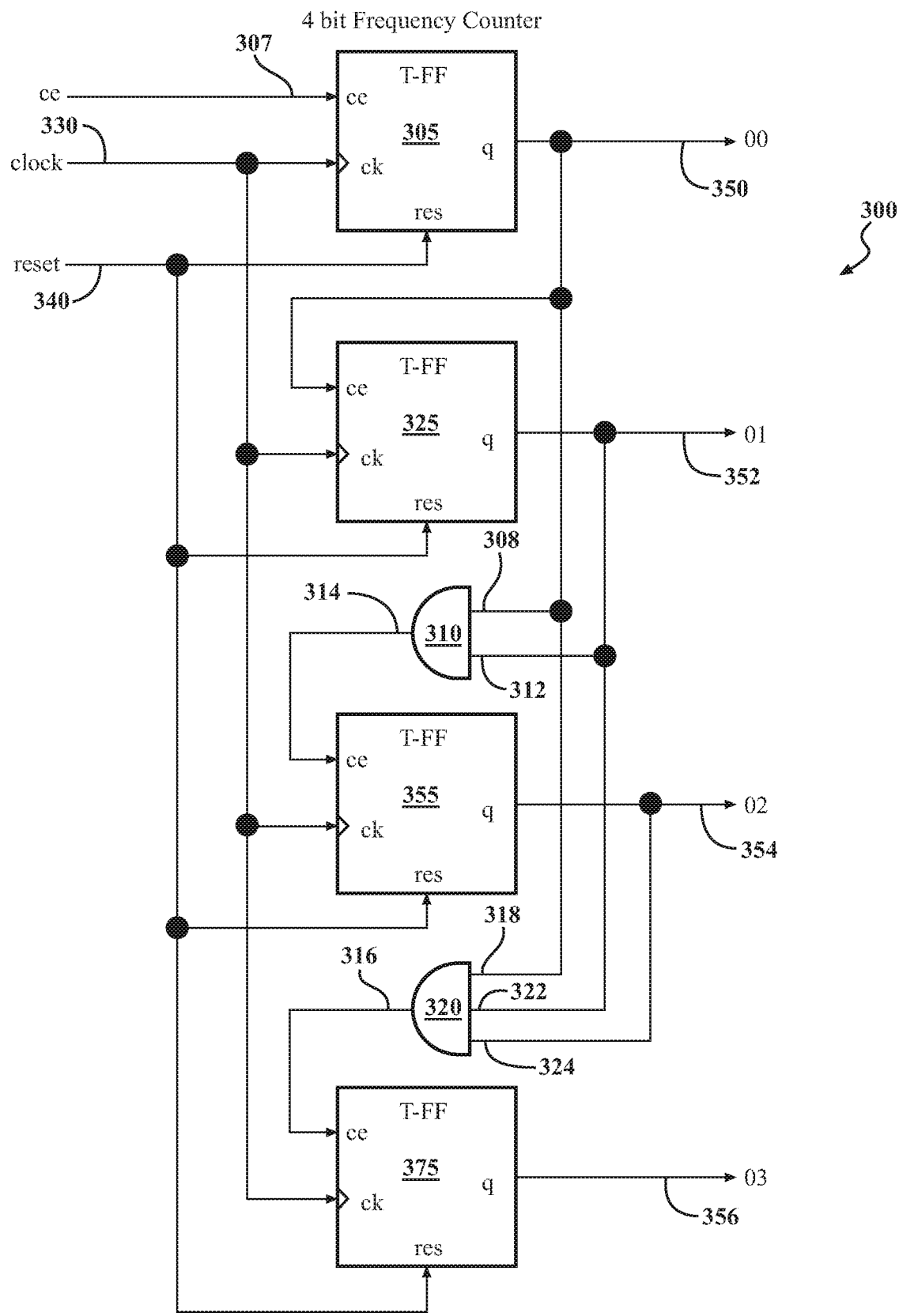
FIG. 3 is a circuit diagram of an exemplary 4-bit binary counter.

The pulse selector inputs 205 and 215 determine the number of pulses present in the output signal 285. For example, the number of pulses in the output signal 285 that may be selected are 1, 2, 4, 8, etc. In one combination of the pulse selector inputs 205 and 215, the output signal 285 may be a continuous pulse. FIG. 3 shows an exemplary 4-bit binary counter circuit that is discussed below following the discussion of FIGS. 4-7. FIGS. 4-7 show various examples of pulse signal output that may be obtained from the embodiments discussed in the present disclosure.

Figure 4:
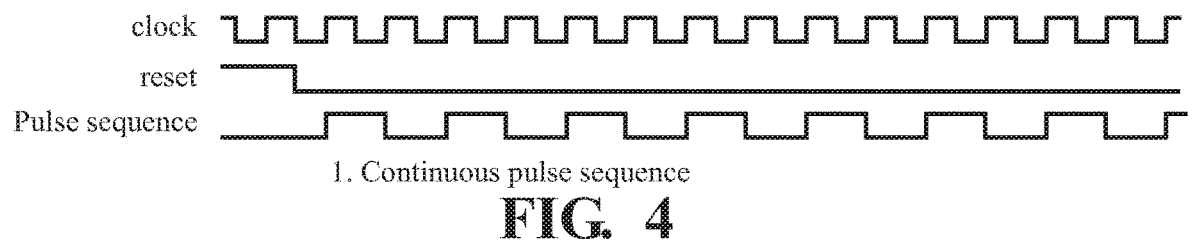
FIG. 4 shows an example of pulse signal output of the PSGC shown in FIG. 2, the continuous pulse output.

FIG. 4 shows an output signal waveform for a given input clock signal and reset signal. These signals are discussed below in reference to FIG. 2. The input clock signal and reset signal of FIG. 4 may be respectively connected to the input clock signal 260 and reset signal 265 of FIG. 2. The reset signal is shown active-high, therefore when the reset signal ends, the PSGC 200 starts providing the output signal 285. If the pulse selector inputs 205, 215 are set to "00", the PSGC 200 would provide a continuous pulse output signal as shown in FIG. 4. The continuous pulse output signal is selected if all the pulse selector inputs are logic "low". The frequency of the continuous output pulse is about half the frequency of the given clock signal. If instead of input signal 220, the other input signal 225, 230 or 235 is connected to 0V, when the pulse selector inputs select 225, 230 or 235 then the output signal 285 would be a continuous output pulse.

Figure 5:
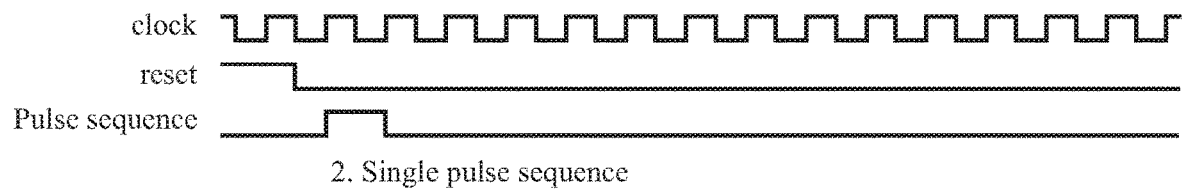
FIG. 5 also shows an example of pulse signal output of the PSGC shown in FIG. 2, single pulse output.

Referring to FIG. 5, another example of the output signal form for a given input clock signal and reset signal is shown. These signals are discussed below in reference to FIG. 2. The input clock signal and reset signal of FIG. 5 may be respectively connected to the input clock signal 260 and reset signal 265 of FIG. 2. The reset signal is shown active-high, therefore when the reset signal ends, the PSGC 200 starts providing the output signal 285. If the pulse selector inputs 205, 215 are set to "01", the PSGC 200 would provide a single pulse output signal as shown in FIG. 5. The frequency of the single output pulse is about half the frequency of the given clock signal.

Figure 6:
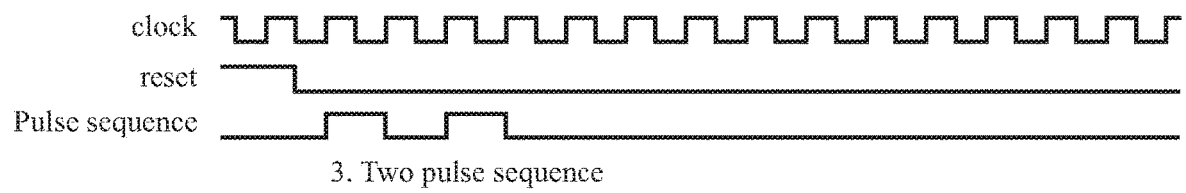
FIG. 6 shows another example of pulse signal output of the PSGC shown in FIG. 2, two pulse output.

Referring to FIG. 6, another example of the output signal form for a given input clock signal and reset signal is shown. These signals are discussed below in reference to FIG. 2. The input clock signal and reset signal of FIG. 6 may be respectively connected to the input clock signal 260 and reset signal 265 of FIG. 2. The reset signal is shown active-high, therefore when the reset signal ends, the PSGC 200 starts providing the output signal 285. If the pulse selector inputs 205, 215 are set to "10", the PSGC 200 would provide a two pulse output signal as shown in FIG. 6. The frequency of the two pulse output signal is about half the frequency of the given clock signal.

Figure 7:
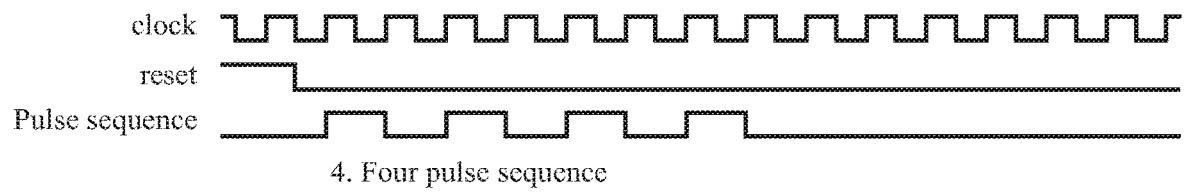
FIG. 7 shows yet another example of pulse signal output of the PSGC shown in FIG. 2, four pulse output.

Referring to FIG. 7, yet another example of the output signal form for a given input clock signal and reset signal is shown. These signals are discussed below in reference to FIG. 2. The input clock signal and reset signal of FIG. 7 may be respectively connected to the input clock signal 260 and reset signal 265 of FIG. 2. The reset signal is shown active-high, therefore when the reset signal ends, the PSGC 200 starts providing the output signal 285. If the pulse selector inputs 205, 215 are set to "11", the PSGC 200 would provide a four pulse output signal as shown in FIG. 7. The frequency of the four pulse output signal is about half the frequency of the given clock signal.

In a variation of the PSGC 200 in FIG. 2, the output signals 280, 270 of the counter circuit 250 may instead provide the input signals 235, 225 of the multiplexer 210. In that case, if the pulse selector inputs 205, 215 are set to "01", the PSGC 200 would provide a four pulse output signal as shown in FIG. 7. If the pulse selector inputs 205, 215 are set to "11", the PSGC 200 would provide a single pulse output signal as shown in FIG. 5. In another variation, if the output signal 280 provides the pulse sequence output for the PSGC 200, then the output pulse will be 10 MHz given that the input clock signal 260 for the counter circuit is 40 MHz. However, the remaining pulse sequence output would be limited to single pulse, two pulse and continuous pulse output signals. In general, one may use larger binary counters such as a CTR5B or CTR6B, among others, and also the larger size multiplexers such as a txmx3 or txmx4, among others, for more selection options.

As noted above, FIG. 3 shows the 4-bit binary counter circuit that may be used in embodiments of the PSGC disclosed in the present disclosure, for example, in the PSGC 10 and 200 shown respectively in FIGS. 1 and 2. The counter circuit 300 consists of four Toggle flip-flop (T-FF) circuits (305, 325, 355, 375) and two AND gates (310, 320). However, it should be understood that this is merely illustrative, and the counter circuit may have a different number of T-FF circuits and AND gates. For example, an arbitrary n-bit binary counter circuit can be constructed with n T-FF circuits and ($2^n-2$) AND gates.

Each of the T-FF circuits (305, 325, 355, 375) takes clock enable signal "ce", input clock signal "ck", reset signal "res" and generates output signal "q". In a T-FF, if the T input is high, the T-FF changes states (i.e. toggles) whenever the clock input is strobed. However, if the T input is low, the T-FF holds the previous value. Moreover, when T is held high, the T-FF divides the input clock frequency by two. For example, if the clock frequency is 40 MHz, the output frequency obtained from the T-FF is 20 MHz. Clock signal 330 and reset signal 340, respectively, provide input clock signal "ck" and reset signal "res" for all the four T-FF circuits (305, 325, 355, 375).

Enable signal 307 provides clock enable signal "ce" for the T-FF 305. When the enable signal 307 is high, the T-FF 305 generates an output signal 00 350. The output signal 00 350 is provided as an input to the clock enable signal "ce" of T-FF 325 and the AND gates 310, 320. Once T-FF 325 is enabled, T-FF 325 generates an output signal 01 352. The output signal 01 352 is provided as an input to both the AND gates 310, 320. The output 314 of the AND gate 310 is provided as an input to the clock enable signal "ce" of T-FF 355. Once T-FF 355 is enabled, T-FF 355 generates an output signal 02 354. The output signal 02 354 is provided as an input to the AND gate 320, which then generates an output 316. The output 316 is provided as an input to the clock enable signal "ce" of T-FF 375. Once T-FF 375 is enabled, T-FF 375 generates an output signal 03 356.

FIG. 3 is discussed below in reference to FIG. 2. In a non-limiting embodiment of PSGC 200, the 4-bit binary counter circuit 300 shown in FIG. 3 may be used as the counter circuit 250 of FIG. 2. In that case, enable signal 307, clock signal 330, reset signal 340, output signal 00 350, output signal 01 352, output signal 02 354 and output signal 03 356 of counter circuit 300, respectively, are equivalent to the enable signal 255, input clock signal 260, reset signal 265, and output signals 285, 280, 275, 270 of the 4-bit binary counter circuit 250 shown in FIG. 2.

Figure 8:
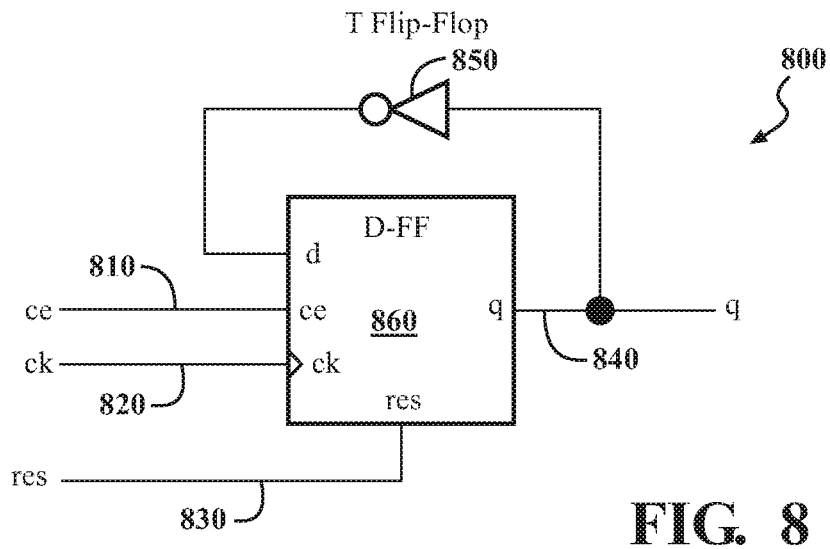
FIG. 8 is a circuit diagram of an example of Toggle flip-flop (T-FF) circuit.

FIG. 8 shows a Toggle flip-flop (T-FF) circuit 800 that may be used as one or more of the T-FF circuits (305, 325, 355, 375) used in the counter circuit 300 of FIG. 3. The T-FF 800 consists of a Data flip-flop (D-FF) circuit 860 and an inverter 850. D-FF 800 takes clock enable signal 810, input clock signal 820, reset signal 830 and data signal to provide an output q 840. The output q 840 is used as the data signal after inverting the signal using the inverter 850.

Figure 9:
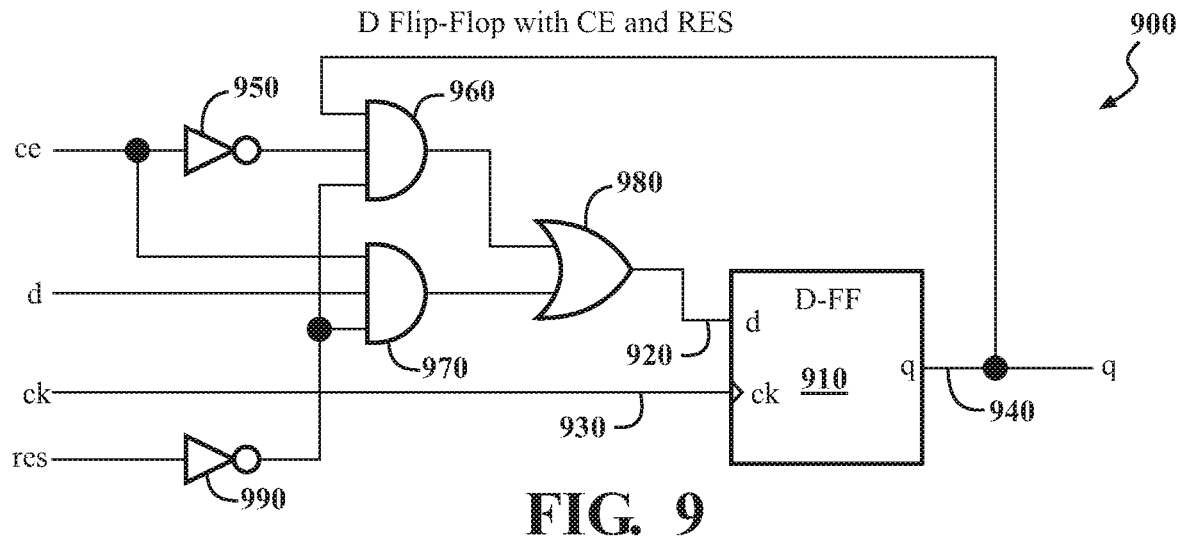
FIG. 9 is a circuit diagram of an example of Data flip-flop (D-FF) circuit with ce and reset inputs.

FIG. 9 shows an exemplary design circuit of a Data flip-flop (D-FF) 900 with "ce" and "res" inputs. The D-FF circuit 900 consists of a D-FF 910, two inverters (950, 990), two AND gates (960, 970) and an OR gate 980. As shown, D-FF circuit 900 with "ce" and "res" inputs, subsequently, is built with a D-FF 910 having only data input "d" 920 and input clock signal "ck" 930. A clock enable signal "ce" acts as an input for the inverter 950 and the AND gate 970. The data signal "d" acts as one of the inputs for AND gate 970. D-FF 910 receives the input clock signal "ck" at 930. Reset signal "res" is inverted by the inverter 990 and the inverted reset signal acts as an input for the AND gates 960, 970. Outputs from AND gates 960, 970 is provided as the input to the OR gate 980. The output of the OR gate 980 is provided as data signal "d" at 920 of D-FF 910. The D-FF generates an output q 940 that also acts as an input for the AND gate 960. The reset signal "res" is a synchronous input signal in this case. However, the T-FF circuit used in a binary counter circuit may be made with an asynchronous reset signal. The asynchronous reset signal is typically called a "clear" signal instead of a reset signal. A simpler D-FF circuit discussed above, with only "d" and "ck" inputs, can be positive edge-triggered or negative edge-triggered. Consequently, the T-FF circuit used in a binary counter circuit can be positive edge-triggered or negative edge-triggered.

Figure 10A:
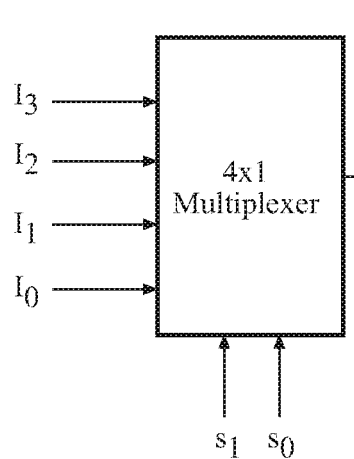
FIG. 10*a* is a circuit diagram of a digital 4-to-1 multiplexer.
Figure 10B:
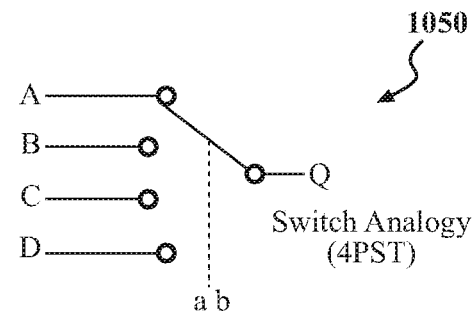
FIG. 10*b* shows a switch analogy for the 4-to-1 multiplexer in FIG. 10*a*.

A multiplexer is a switch to select one of several analog or digital input signals and pass the selected input signal to a single output line. A multiplexer of $2^n$ inputs has n select lines, which are used to select which input line to send to the output line. The multiplexer can be considered as a multiple-input, single output switch. A circuit diagram of an example of a 4-to-1 multiplexer is shown in FIG. 10a. The 4-to-1 multiplexer 1010 has four inputs ($I_3$, $I_2$, $I_1$, $I_0$) and two selector lines ($s_1$, $s_0$). The 4-to-1 multiplexer 1010 selects one of the four inputs based on the selector lines and connects the selected line to the output line Y. FIG. 10b shows a switch analogy of a digital multiplexer. FIG. 10b shows a four-pole single-throw (4PST) switch, four inputs (A, B, C, D), an output Q and a movable link ab. One of the four inputs (A, B, C, D) is connected to the output line Q based on the position of the movable link ab.

There are many ways to implement a 4-to-1 multiplexer 1010. FIG. 11a is an exemplary detailed diagram of a digital 4-to-1 multiplexer circuit. The 4-to-1 multiplexer 1110 consists of four AND gates (1120, 1130, 1140, 1150), three inverters (1170, 1180, 1190) and an OR gate 1160. The 4-to-1 multiplexer 1110 has four inputs ($I_0$, $I_1$, $I_2$, $I_3$), two selector inputs ($S_1$, $S_0$) and provides an output Z based on the selectors input. Each of the inputs $I_0$, $I_1$, $I_2$, $I_3$ is connected respectively to the AND gates 1120, 1130, 1140, 1150. Selector input $S_1$ is connected to the AND gates 1140, 1150. Selector input $S_1$ is inverted using inverter 1180 and the output of the inverter 1180 is connected to the AND gates 1120, 1130. Selector input $S_0$ is connected to the AND gates 1130, 1150. Selector input $S_0$ is inverted using inverter 1190 and the inverted input is connected to the AND gate 1190. Similarly, selector input $S_0$ is inverted using inverter 1170 and the inverted input is connected to the AND gate 1120. Outputs from all the four AND gates (1120, 1130, 1140, 1150) are connected to the OR gate that provides Z as the output.

FIG. 11b also shows a truth table for the 4-to-1 multiplexer 1110. For example, the state of selector inputs ($S_0$, $S_1$) as 00, 01, 10, 11 respectively provides $I_0$, $I_1$, $I_2$, $I_3$ as output Z. However, it should be understood that this is merely illustrative, and a PSGC may consist of multiplexers with more inputs than the 4-to-1 multiplexer 1110.

As noted above, the number of pulses in the pulse sequence output generated by the PSGC 200 can be 1, 2, 4, 8, 16 etc. The number of pulses generated in the sequence is in power of two number, except for the continuous pulse sequence. Another embodiment of the PSGC is shown in FIG. 12. The PSGC 1200 shown in FIG. 12 is similar to the PSGC 200 but also has two integer-number detector circuits (i.e. number 3 detector circuit "det3" 1295 and number 5 detector circuit "det5" 1290). The resulting PSGC 1200 is capable of generating 1, 3, 5 and continuous pulse sequences. A PSGC according to this disclosure may use a plurality of integer-number detector circuits. The integer-number detector circuits enable a PSGC to generate an integer-numbered pulse sequence output. In non-limiting integer-number detector circuit examples (not shown), a number 7 detector circuit, a number 9 detector circuit and a number 11 detector circuit if used in the PSGC according to this disclosure would respectively enable it to generate 7, 9 and 11 pulse sequence output.

As noted above, FIG. 12 shows the embodiment of a PSGC with four outputs. Referring now to FIG. 12, the PSGC 1200 consist of four functional circuit modules, i.e. a 4-to-1 multiplexer 1210, a 4-bit binary counter circuit 1250 and two integer-number detector circuits det3, det5. In FIG. 12, the 4-to-1 multiplexer 1210 is labeled as "txmx2" and the 4-bit binary counter circuit 250 is labeled as "CTR4B". The multiplexer 1210 takes input signals (1220, 1225, 1230, 1235) and pulse selector inputs (1205/s1, 1215/s0) and generates an output signal 1240.

The input signal 1220 takes an input clock signal 1260. The selection made by the multiplexer 1210 between the input signals (1220, 1225, 1230, 1235) is determined by the pulse selector inputs (1205/s1, 1215/s0). Therefore, one of the input signals (1220, 1225, 1230, 1235) is selected and forwarded as the output signal 1240 based on the pulse selector inputs (1205/s1, 1215/s0).

The counter circuit 1250 takes clock enable signal "ce" 1255, input clock signal 1260, reset signal 1265 and generates output signals 1270, 1275, 1280 and 1285. The output signal 1285 provides a pulse sequence output for the PSGC 1200. All the output signals 1270, 1275, and 1280 provide input signals for the det3 and det5. In addition, the output signal 1280 provides an input signal 1225 for the multiplexer 1225. Outputs from det3 and det5 respectively are provided as input signals 1230 and 1235 for the multiplexer 1210. However, it should be understood that this is merely illustrative, and the other output signals may instead be used for providing the pulse sequence out. For example, in some embodiments of the PSGC 1200, the output signals 1270, 1275 or 1280 may provide the pulse sequence output. In that case, the remaining connections between the counter circuit 1250, det3, det5 and the multiplexer 1210 remain unchanged. As shown in FIG. 12, the output signal 1240 of the multiplexer 1210 is connected to the clock enable signal "ce" 1255 through an inverter gate 1245.

The PSGC 1200 uses a counter circuit 1250 with the clock enable signal "ce" as an active-high signal input. Therefore, the inverter gate 1245 is required to connect the output signal 1240 of the multiplexer 1210 to the clock enable signal "ce" 1255 through the inverter gate 1245. However, it should be understood that this is merely illustrative, and other embodiments of the PSGC 1200 may not require the inverter gate 1245. For example, a counter circuit 1250 in an embodiment of the PSGC 1200 may present the clock enable signal "ce" as an active-low signal input, and therefore, would not require the inverter gate 1245.

In some embodiments, the PSGC 1200 divides the input clock signal 1260 by half and generates the output signal 1285. For example, the 20 MHz output signal 1285 is generated from the 40 MHz input clock signal 1260 and the 10 MHz output signal 1285 is generated from the 20 MHz input clock signal 1260. The reset signal 1265 determines the starting of the output signal 1285. In a non-limiting example, the reset signal 1265 is initially active-high and when the reset signal 1265 ends, the output signal 1285 starts. In some embodiments, the reset signal 1265 may initially be held active-low and when the reset signal 1265 turns high, the output signal 1285 starts.

The pulse selector inputs 1205 and 1215 determine the number of pulses present in the output signal 1285. For example, the number of pulses in the output signal 1285 that may be selected are 1, 3, 5, etc. In one combination of the pulse selector inputs 1205 and 1215, the output signal 1285 may be a continuous pulse. As discussed above, FIG. 3 shows an exemplary 4-bit binary counter circuit. FIGS. 4-5 show two examples of a pulse signal output that may be obtained from the embodiments discussed in the present disclosure.

FIG. 4 shows an output signal waveform for a given input clock signal and reset signal. These signals are discussed below in reference to FIG. 12. The input clock signal and reset signal of FIG. 4 may be respectively connected to the input clock signal 1260 and reset signal 1265 of FIG. 12. The reset signal is shown active-high, therefore when the reset signal ends, the PSGC 1200 starts providing the output signal 1285. If the pulse selector inputs 1205, 1215 are set to "00", the PSGC 1200 would provide a continuous pulse output signal as shown in FIG. 4. The continuous pulse output signal is selected if all the pulse selector inputs are logic "low". The frequency of the continuous output pulse is about half the frequency of the given clock signal. If instead of the input signal 1220, the other input signal 1225, 1230 or 1235 is connected to 0V, when the pulse selector inputs select 1225, 1230 or 1235 then the output signal 1285 would be a continuous output pulse.

Referring to FIG. 5, another example of the output signal form for a given input clock signal and reset signal is shown. These signals are discussed below in reference to FIG. 12. The input clock signal and reset signal of FIG. 5 may be respectively connected to the input clock signal 1260 and reset signal 1265 of FIG. 12. The reset signal is shown active-high, therefore when the reset signal ends, the PSGC 1200 starts providing the output signal 1285. If the pulse selector inputs 1205, 1215 are set to "01", the PSGC 1200 would provide a single pulse output signal as shown in FIG. 5. The frequency of the single output pulse is about half the frequency of the given clock signal.

The input clock signal and reset signal may be respectively connected to the input clock signal 1260 and reset signal 1265 of FIG. 12. If the reset signal is active-high, and the reset signal ends, the PSGC 1200 starts providing the output signal 1285. If the pulse selector inputs 1205, 1215 are set to "10", the PSGC 1200 would provide a three pulse output signal (not shown). The frequency of the three pulse output is about half the frequency of the given clock signal.

Similarly, the input clock signal and reset signal may be respectively connected to the input clock signal 1260 and reset signal 1265 of FIG. 12. If the reset signal is active-high, and the reset signal ends, the PSGC 1200 starts providing the output signal 1285. If the pulse selector inputs 1205, 1215 are set to "11", the PSGC 1200 would provide a five pulse output signal (not shown). The frequency of the five pulse output is about half the frequency of the given clock signal.

In a variation of the PSGC 1200 in FIG. 12, the output signal 1280 and output from det5 may instead provide the input signals 1235, 1225 of the multiplexer 1210—that is if 1225 and 1235 connections are swapped. In that case, if the pulse selector inputs 1205, 1215 are set to "01", the PSGC 200 would provide a five pulse output signal (not shown). If the pulse selector inputs 1205, 1215 are set to "11", the PSGC 1200 would provide a single pulse output signal as shown in FIG. 5. In another variation, if the output signal 1280 provides the pulse sequence output for the PSGC 1200, then the output pulse will be 10 MHz given that the input clock signal 1260 for the counter circuit is 40 MHz. However, the remaining pulse sequence output would be limited to single pulse, three pulse and continuous pulse output signals. In general, one may use larger binary counters such as a CTR5B or CTR6B, among others, and also the larger size multiplexers such as a txmx3 or txmx4, among others, for more selection options. According to this disclosure, the number of pulses in the output pulse sequence in the PSGC 200 and the PSGC 1200 are dynamically selectable from the predetermined set of options.

Figure 13:
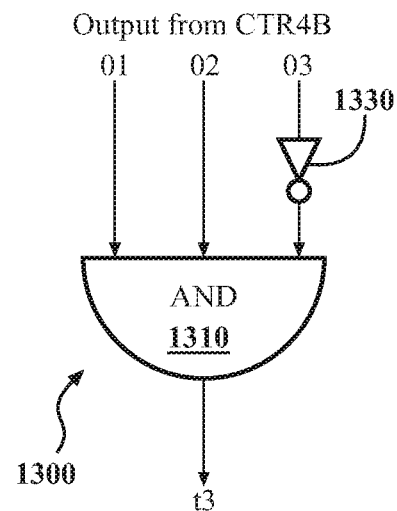
FIG. 13 is a detector circuit diagram.

FIG. 13 shows an integer-number detector circuit det3 1300 that may be used in the PSGC 1200 shown in FIG. 12. The det3 1300 consists of a 3-input AND gate 1310 and one inverter 1330. An AND gate 1310 receives three inputs 01, 02, 03 and provides an output t3. The input 03 is first inverted using the inverter 1330 before being used as an input for the AND gate 1310. FIG. 13 is discussed below in reference to FIG. 12. If the det3 1300 is used in the PSGC 1200, the output t3 may provide an input 1230 for the multiplexer 1210. The output signals 1270, 1275, 1280 of the counter circuit 1250 are respectively connected as inputs 03, 02, 01 of the det3 1300. The integer-number detector circuit det3 1300 would enable the PSGC 1200 to generate a three pulse sequence output. It should be understood that this is merely illustrative, and the other components/gates or their combination may instead be used to execute similar signal processing.

In FIG. 13, the det3 circuit provides an output t3=(01), (02) and (not 03). In other words, det3 enables generating a three-pulse output sequence. This may be changed to det4 circuit (not shown) if the output t3=(not 01), (not 02) and (03). Alternatively, det3 may be changed to det5 if the output t3=(01), (not 02) and (03). Det3 may also be changed to det6 if t3=(not 01), (02) and (03). In some embodiments, det3 may be changed to det7 if t3=(01), (02) and (03). The PSGC 1200 may generate any positive integer number of pulses, if different combinations of the det circuits are used. In some embodiments of the PSGC, an odd number and/or an even number of pulses may be generated as the output pulse sequence. The PSGCs disclosed herein may be configured for generating continuous pulses as well as any positive integer number of pulses as an output sequence.

Figure 14:
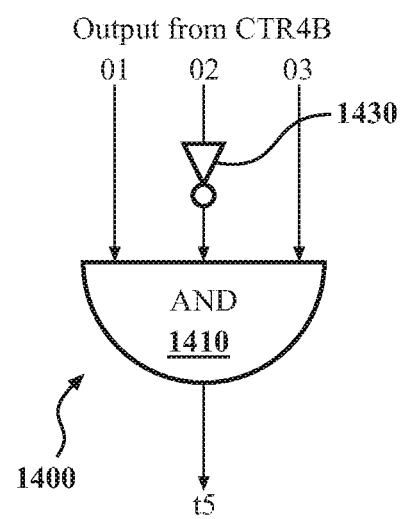
FIG. 14 is another detector circuit diagram.

FIG. 14 shows an integer-number detector circuit det5 1400 that may be used in the PSGC 1200 shown in FIG. 12. The det5 1400 consists of a 3-input AND gate 1410 and one inverter 1430. An AND gate 1410 receives three inputs 01, 02, 03 and provides an output t5. The input 02 is first inverted using the inverter 1430 before being used as inputs for the AND gate 1410. FIG. 14 is discussed below in reference to FIG. 12. If the det5 1400 is used in the PSGC 1200, the output t5 may provide an input 1235 for the multiplexer 1210. The output signals 1270, 1275, 1280 of the counter circuit 1250 are respectively connected as inputs 03, 02, 01 of the det5 1400. The integer-number detector circuit det5 1400 would enable the PSGC 1200 to generate a five pulse sequence output. It should be understood that this is merely illustrative, and the other components/gates or their combination may instead be used to execute similar signal processing.

Figure 15:
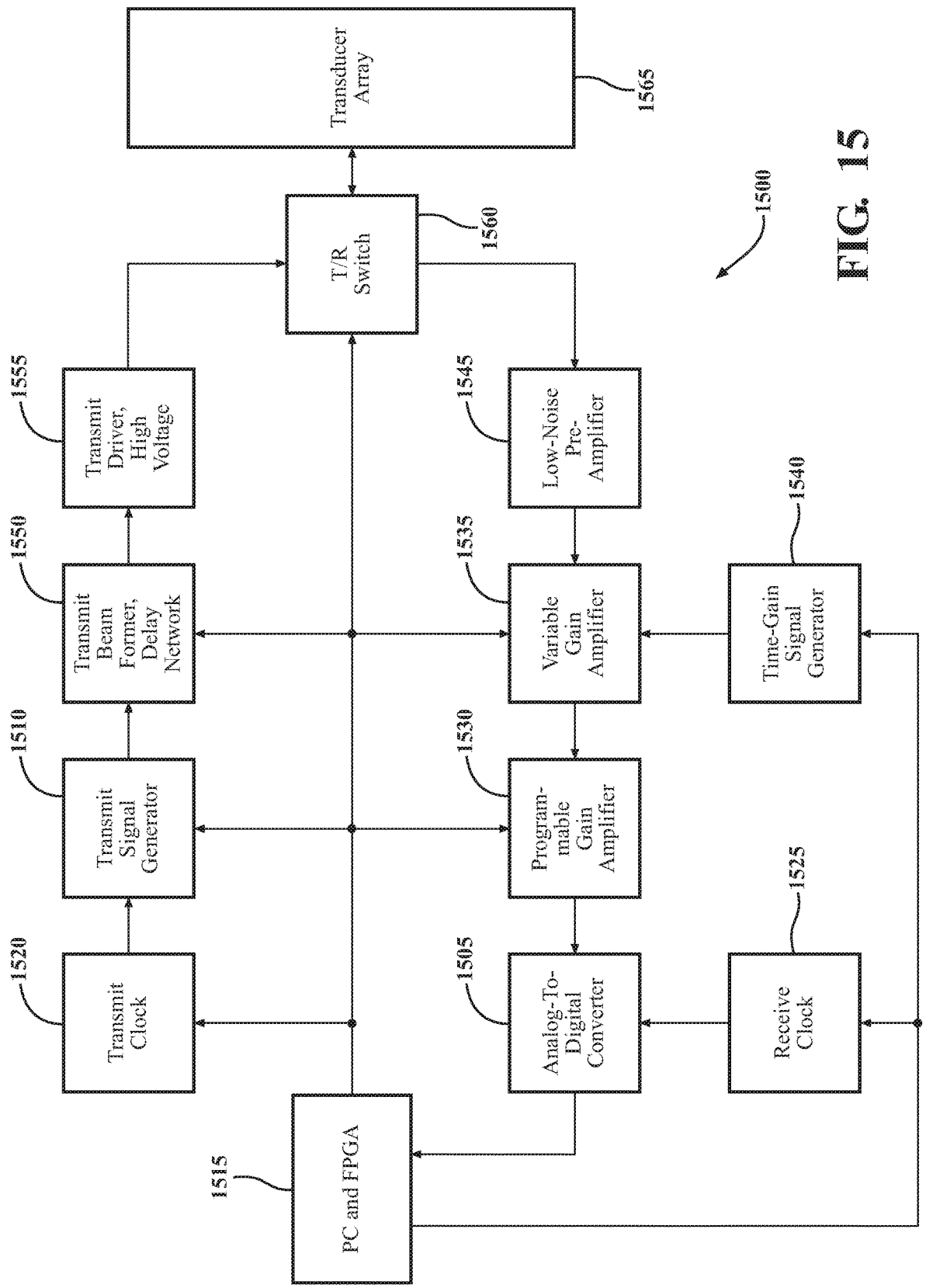
FIG. 15 is a block diagram of an ultrasound imaging system.

There are many applications for the embodiments of a PSGC as disclosed herein. The proposed technology is discussed herewith in detail in reference to an ultrasound probe. However, it should be understood that this is merely illustrative, and the proposed technology has other applications and uses. Non-limiting examples include a general purpose trigger signal generator, general purpose pulse burst generator, one-shot timer, strobe light etc. FIG. 15 is a block diagram of an ultrasound imaging system 1500, wherein the above discussed embodiments of the PSGC may be used as signal generator. It should be noted that the ultrasound imaging system 1500 is discussed herein for illustration and the ultrasound imaging system using the PSGC may have more, less or alternative components than those shown in FIG. 15.

The ultrasound imaging system 1500 measures the reflectivity of tissue to sound waves. It can also measure velocity of moving objects, e.g. blood flow. The system 1500 provides a non-invasive imaging system without exposing a person to any radiation. The system 1500 consists of a transducer array 1565 that is used both as a transmitter and a receiver. In a transmission mode, the transmitter converts an oscillating voltage into mechanical vibrations, which transmits a series of sound pressure waves into the body. In a receiving mode, the receiver converts backscattered sound pressure waves into electrical signals. In a non-limiting example, the transducer array 1565 is comprised of an array of piezoelectric transducer elements that transmit focused energy into the body and receive the resulting reflections. The transducer array 1565 may have 32 to as many as 512 elements and may operate at frequencies from 1 MHz to 15 MHz.

The ultrasound imaging system 1500 also has a transmitter/receiver (T/R) switch 1560. As noted above, the transducer array 1565 may have 32 to as many as 512 elements, but the system may have fewer transmitters and receivers than the number of available transducer elements. In these cases, a T/R switch 1560 located in the system 1500 is used as multiplexer to connect a specific transducer element to a specific transmitter/receiver pair.

The ultrasound imaging system 1500 also has a Personal Computer and Field Programmable Gate Array (PC/FPGA) 1515 with one or more microprocessors that directs the operation of the entire system. The PC 1515 senses the settings of the controls and input devices, such as the keyboard, and executes the commands to control the hardware to function in the desired mode. It orchestrates the necessary setup of the transmit and receive beamformers 1550 as well as the signal processing, display, and output functions. Another important duty of the computer is to regulate and estimate the level of acoustic output in real time.

The ultrasound imaging system 1500 also has a transmit clock 1520 that provides an input clock signal for various components of the system 1500. As discussed above, the PSGC 200 and 1200 both respectively receive input clock signals 260 and 1260. The transmit clock 1520 provides an input signal to the transmit signal generator 1510. Various embodiments of the transmit signal generators (i.e. PSGC 200 and 1200) are discussed above.

The transmit signal generator 1510 transmits its output signal to a transmit beamformer 1550 that typically generates the necessary digital transmit signals with the proper timing and phase to produce a focused transmit signal. The ultrasound imaging system 1500 may generate complex transmit waveforms using an arbitrary waveform generator to optimize image quality. In these cases, the transmit beamformer 1550 may generate digital 8-bit to 10-bit words at rates of approximately 40 MHz to produce the required transmit waveform.

A high-voltage transmit driver 1555 conditions the transmit waveform from the transmit beamformer 1550 and transmits the conditioned transmit waveform to the T/R switch 1560. As discussed above, a T/R switch 1560 located in the system 1500 connects a specific transducer element to a specific transmitter/receiver pair.

The T/R switch 1560 is connected to a Low Noise Pre-Amplifier (LNA) 1545. It is desirable that the LNA 1545 have excellent noise performance and sufficient gain. The transducer element from the transducer array 1565 may be directly/indirectly connected to the LNA 1545 through a relatively long coaxial transducer cable terminated into relatively low impedance at the LNA's 1545 input. The signal received from the transducer array 1565 is amplified by the LNA 1545 and later conditioned by a variable gain amplifier 1535 and a programmable gain amplifier 1530.

During the ultrasound send-receive cycle, the magnitude of reflected signal depends on the depth of penetration. The purpose of Time Gain Control (TGC) is to normalize the signal amplitude with time; compensating for depth. When the image is displayed, similar material should have similar brightness, regardless of depth and this is achieved by "Linear-in-dB" Gain, which means the decibel gain is a linear function of the control voltage. A time gain signal generator 1540 is connected to variable gain amplifier 1535 for TGC.

The signal from the programmable gain amplifier 1505 is then transmitted to an analog to digital converter to convert the analog amplified received signal into a digital format for further processing to the PC 1515. The analog to digital converter 1505 receives an input from a receive clock 1525. Various components of the ultrasound imaging system 1500 are connected to the PC 1515 and are not discussed in detail here.

Additional features and functionality of the ultrasound imaging system 1500 should generally be understood and are not discussed in further detail herein. Additionally, it should be understood that the various components described with respect to the transmit signal generator are merely illustrative. Accordingly, the ultrasound imaging system 1500 may include additional components, fewer components, alternative components, and/or the like without departing from the scope of the present disclosure.

Figure 16:
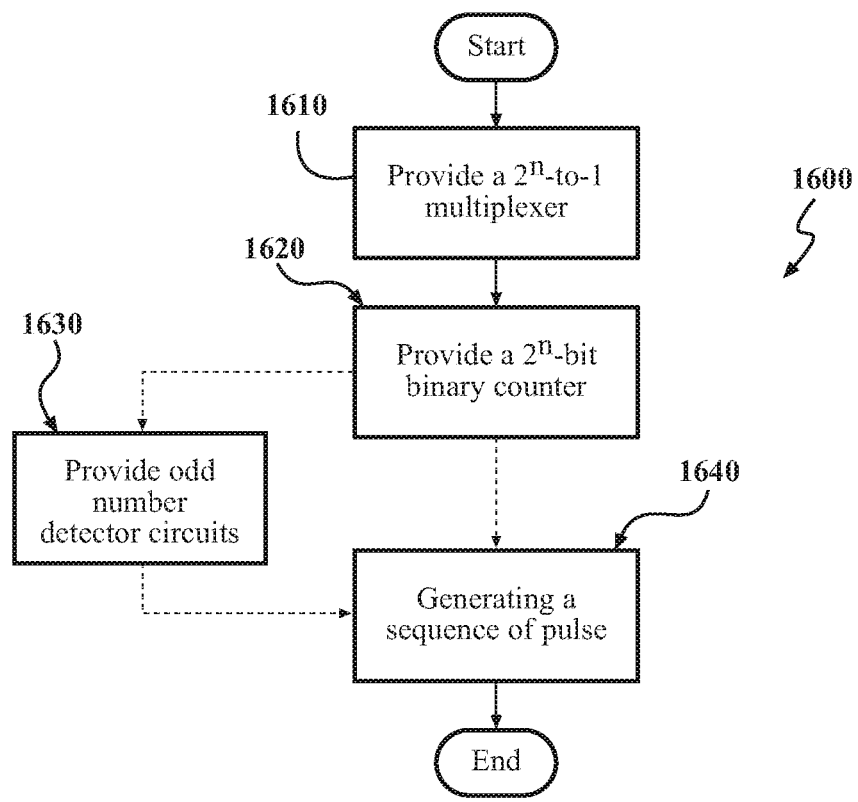
FIG. 16 is a flow diagram of methods to generate sequence of pulses.

Referring now to FIG. 16, a flow diagram is provided showing methods of generating odd or even numbers or a continuous sequence of pulses. An embodiment of method 1600 of generating a sequence of pulses, includes a plurality of steps. Step 1610 includes providing a $2^n$-to-1 multiplexer having $2^n$ input lines, n selector lines and an output line providing an output of the multiplexer, connecting one of the $2^n$ input lines to ground or zero potential, connecting the n selector lines to a selector signal, and the multiplexer selecting one of the $2^n$ input lines as the output of the multiplexer based on the selector signal.

Step 1620 includes providing a $2^n$-bit binary counter having a clock signal input line, a reset signal input line, a clock enable line, and $2^n$ output lines, connecting the clock signal input line to a clock signal input, connecting the reset signal input line to a reset signal input, connecting the clock enable line to the output line of the multiplexer for providing the output of the multiplexer as an input signal for the clock enable line, one of the $2^n$ output lines providing a sequence of pulse as an output of the transmit signal generator, and connecting each of the remaining $2^n$ output lines of the binary counter to one of the remaining $2^n$ input lines of the multiplexer. Step 1640 is then followed to generate a sequence of 1, 2, 4, 8, ... n pulses. According to step 1640, the output of the transmit signal generator is providing a continuous pulse or an N pulse sequence as the output based on the selector signal and the reset signal input initiating generation of the sequence of pulses, wherein $N \leq 2^n$ and n is an integer.

If an odd number (i.e. 1, 3, 5, ... n), another integer (e.g. 6, 12, 14; numbers that are not obtained by using power of 2) or a continuous number of pulses are to be generated, then the method 1600 is followed as discussed below. The numbers discussed above are identified herein as positive integer numbers. An embodiment of method 1600 for generating a positive integer number of pulses at 1610 includes the steps of providing a $2^n$-to-1 multiplexer having $2^n$ input lines, n selector lines and an output line providing an output of the multiplexer, connecting one of the $2^n$ input lines to ground or zero potential, and connecting the n selector lines to a selector signal, the multiplexer selecting one of the $2^n$ input lines as the output of the multiplexer based on the selector signal.

At 1620, the method includes providing a $2^n$ bit binary counter having a clock signal input line, a reset signal input line, a clock enable line, and $2^n$ output lines, connecting the clock signal input line to a clock signal input, connecting the reset signal input line to a reset signal input, connecting the clock enable line to the output line of the multiplexer providing the output of the multiplexer as an input signal for the clock enable line, one of the $2^n$ output lines providing a sequence of pulse as an output of the transmit signal generator, and connecting another of the $2^n$ output lines of the binary counter to one of the $2^n$ input lines of the multiplexer.

At 1630, the method includes providing ($2^n$–2) integer-number detector circuits and connecting each of the $2^n$ output lines of the binary counter to each of the integer-number detector circuits as an input, each of the integer-number detector circuits having an output line connected to one of the remaining $2^n$ input lines of the multiplexer. Integer-number detector circuits 1295, 1290 are discussed above in reference to FIG. 12. Integer-number detector circuits 1300, 1400 are discussed above in reference to FIGS. 13 and 14. At 1640, the method includes that the output of the transmit signal generator provides a continuous pulse or an N pulse sequence as the output based on the selector signal and the reset signal input initiating generation of the sequence of pulses, wherein $N \leq 2^n$, n is an integer and N is a positive integer number.

Figure 17:
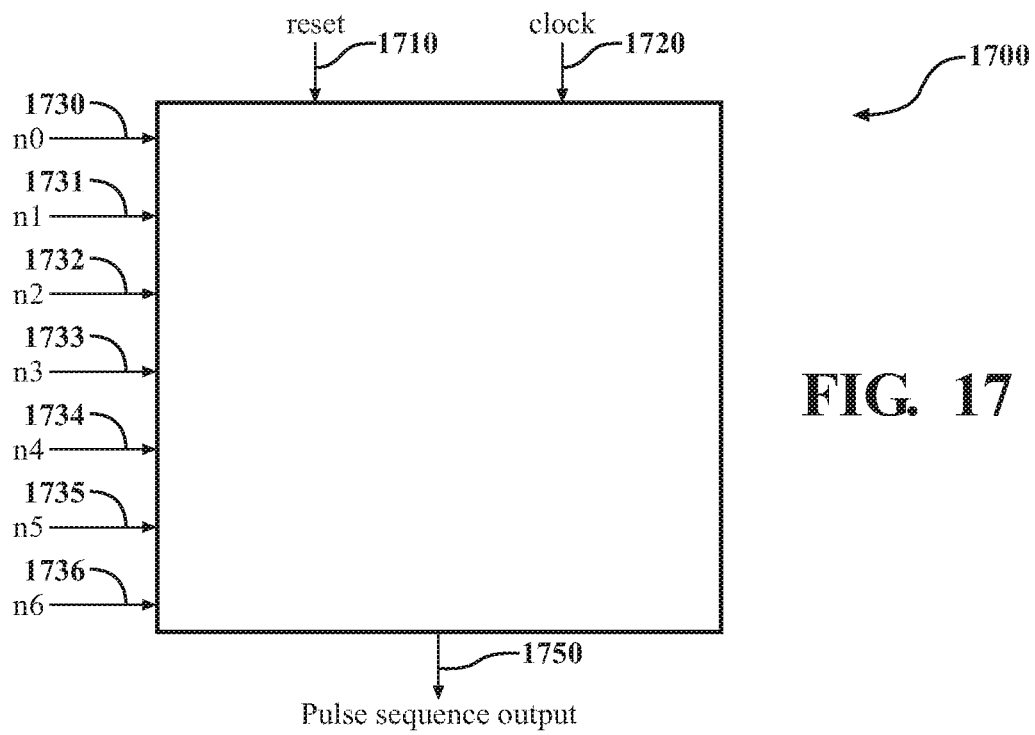
FIG. 17 is a block diagram of another embodiment of a pulse sequence generator circuit (PSGC) according to this disclosure.

FIG. 17 is a block diagram of another embodiment of a pulse sequence generator circuit (PSGC) 1700 according to this disclosure. Referring now to FIG. 17, the PSGC 1700 takes an input clock signal 1720, pulse selector inputs n0 1730, n1 1731, n2 1732, n3 1733, n4 1734, n5 1735, and n6 1736 and generates a pulse sequence output 1750 depending on a trigger signal 1710, or a reset signal. The PSGC 1700 divides the input clock signal 1720 by half and generates the pulse sequence output 1750. For example, a 20 MHz pulse sequence output 1750 is generated from a 40 MHz input clock signal and a 10 MHz pulse sequence output 1750 is generated from a 20 MHz input clock signal. The trigger signal 1710 determines the starting of the pulse sequence output 1750. In a non-limiting example, the trigger signal 1710 is initially active-high and when the trigger signal 1710 ends, the pulse sequence output 1750 starts. In some embodiments, the trigger signal 1710 may initially be held active-low and when the trigger signal 1710 turns high, the pulse sequence output 1750 starts.

The pulse selector inputs n0 1730, n1 1731, n2 1732, n3 1733, n4 1734, n5 1735, n6 1736, and n7 1737 determine the number of pulses present in the pulse sequence output 1750. For example, the number of pulses in the pulse sequence output 1750 may be between 0 and 127. In one combination of the pulse selector n0 1730, n1 1731, n2 1732, n3 1733, n4 1734, n5 1735, n6 1736, and n7 1737, the pulse sequence output 1750 may be a continuous pulse.

Figure 18:
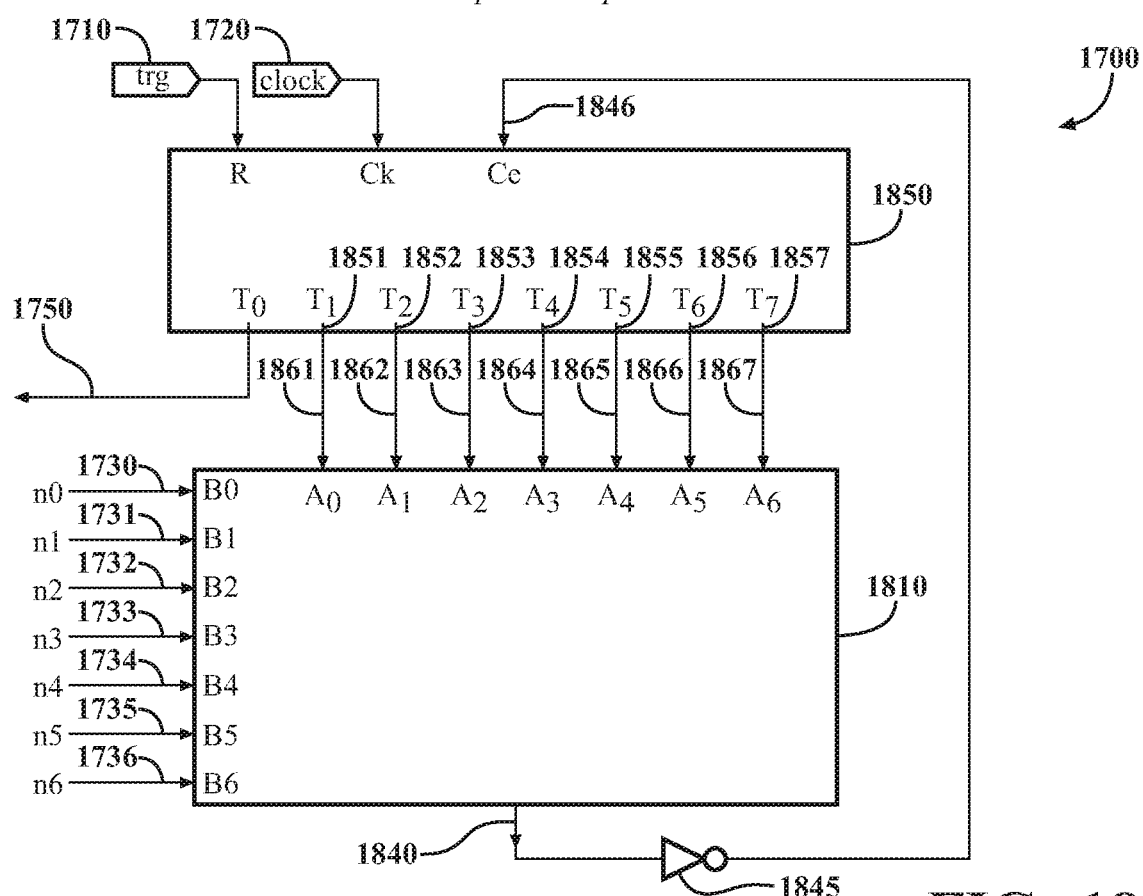
FIG. 18 shows an embodiment of the PSGC that is able to generate up to 127 pulses.

FIG. 18 shows an embodiment of the PSGC 1700 that is able to generate up to 127 pulses. Referring now to FIG. 18, the PSGC 1700 consist of two functional circuit modules, i.e. a 7-bit binary comparator circuit 1810 and an 8-bit binary counter circuit 1850. The 7-bit binary comparator circuit 1810 receives input signals (1861, 1862, 1863, 1864, 1865, 1866, 1867) and input signals n0 1730, n1 1731, n2 1732, n3 1733, n4 1734, n5 1735, and n6 1736 and generates an output signal 1840.

The 7-bit binary comparator circuit 1810 compares the signals (1861, 1862, 1863, 1864, 1865, 1866, 1867) and the input signals n0 1730, n1 1731, n2 1732, n3 1733, n4 1734, n5 1735, and n6 1736 and outputs an output signal 1840.

The 8-bit binary counter circuit 1850 takes a clock enable signal 1846, the input clock signal 1720, the trigger signal 1710 and generates output signals 1750, 1851, 1852, 1853, 1854, 1855, 1856, and 1857. The output signal 1750 provides a pulse sequence output for the PSGC 1700. The remaining output signals 1851, 1852, 1853, 1854, 1855, 1856, and 1857 respectively correspond to input signals 1861, 1862, 1863, 1864, 1865, 1866, and 1867 for the multiplexer 210. As shown in FIG. 18, the output signal 1840 of the 7-bit binary comparator circuit 1810 is connected to the clock enable signal 1846 through an inverter gate 1845.

PSGC 1700 uses the 8-bit binary counter circuit 1850 with clock enable signal as an active-high signal input. Therefore, the inverter gate 1845 is required to connect the output signal 1840 of the 7-bit binary comparator circuit 1810 to the clock enable signal 1846 through the inverter gate 1845. However, it should be understood that this is merely illustrative, and other embodiments of PSGC 1700 may not require the inverter gate 1845. For example, the 8-bit binary counter circuit 1850 in an embodiment of PSGC 1700 may present the clock enable signal as an active-low signal input, and therefore, would not require inverter gate 1845.

In some embodiments, the PSGC 1700 divides the input clock signal 1720 by half and generates the output signal 1750. For example, a 20 MHz output signal 1750 is generated from a 40 MHz input clock signal 1720 and a 10 MHz output signal 1750 is generated from a 20 MHz input clock signal 1720. The trigger signal 1710 determines the starting of the output signal 1750. In a non-limiting example, the trigger signal 1710 is initially active-high and when the trigger signal 1710 ends, the output signal 1750 starts. In some embodiments, the trigger signal 1710 may initially be held active-low and when the trigger signal 1710 turns high, the output signal 1750 starts.

Figure 21:
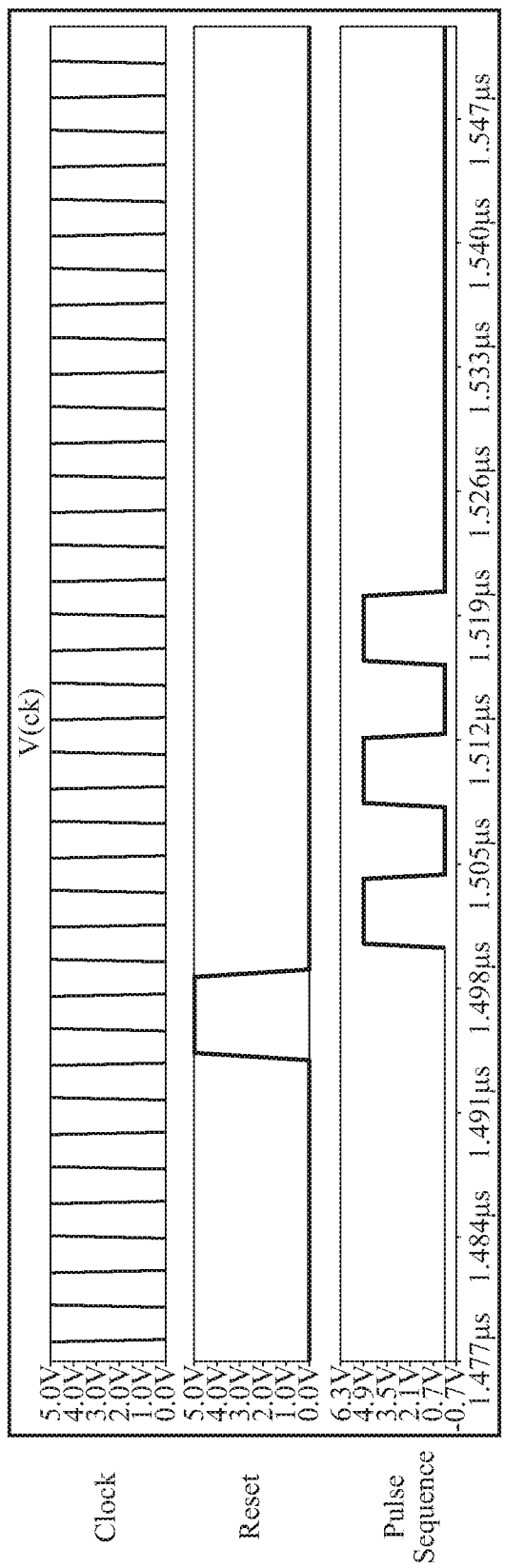
FIG. 21 shows an example of pulse signal output of the PSGC shown in FIG. 17.

The pulse selector inputs n0 1730, n1 1731, n2 1732, n3 1733, n4 1734, n5 1735, and n6 1736 determine the number of pulses present in the output signal 1750. For example, FIG. 21 shows three pulse generation with input clock signal 1720 (shown as V(ck) in FIG. 21) receiving a 250 MHz clock signal, with input rest signal 1710 receiving a trigger signal at 1.494 microsecond, and with input signals n6 through n0 receiving binary number 0000011, or 3 (that is, n6=0V, n5=0V, n4=0V, n3=0V, n2=0V, n1=5V, and n0=5V). The input signals n6 through n0 represent a 7-bit binary number, n6 is the most significant bit (MSB) and n0 is the least significant bit (LSB). The output signal shows a pulse sequence including three pulses after the input trigger signal trg. As another example, FIG. 22 shows 65 pulse generation with input signals n6 through n0 receiving binary number 1000001, or 65 (that is, n6=5V, n5=0V, n4=0V, n3=0V, n2=0V, n1=0V, and n0=5V).

Figure 22:
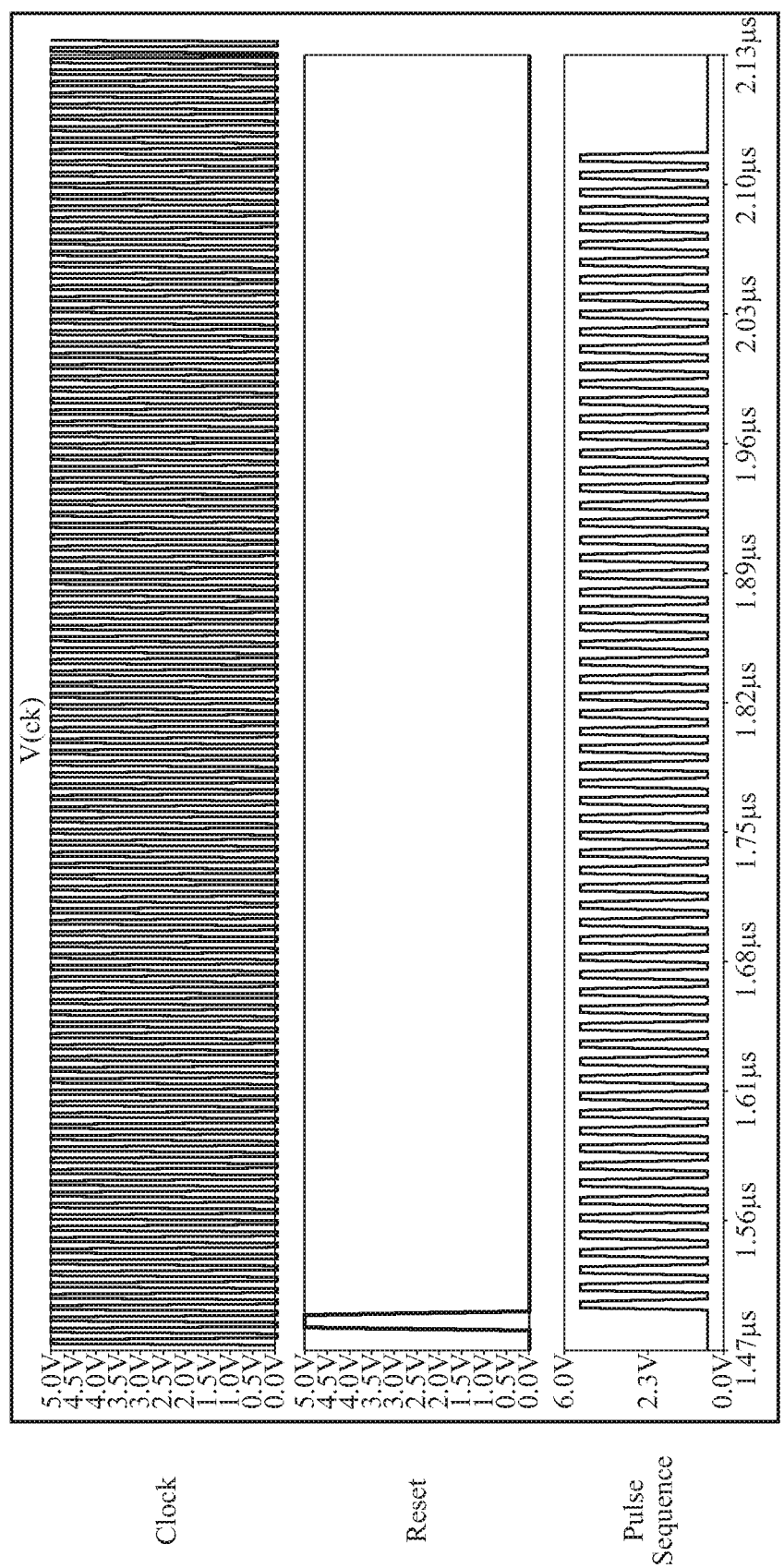
FIG. 22 shows an example of pulse signal output of the PSGC shown in FIG. 17.

As illustrated in FIGS. 21 and 22, the reset signal must be a logic high (e.g., 5V) during a positive edge of the clock signal, completely containing a positive edge. Furthermore, the trigger input signal may be logic high for a longer period of time, containing any number of positive edges of the clock signal. The output signal pulse begins on the immediately following positive edge of the clock signal, after the trigger input signal returns to logic low (0V in this example).

While FIGS. 21 and 22 illustrate 5V logic, the present pulse sequence generator circuit may work for any other logic technology such as 3.3V logic, 1.0V logic, 0.4V logic, etc. In addition, while FIGS. 21 and 22 illustrate using a 250 MHz clock signal, the present pulse sequence generator circuit may work for much faster clock signals with faster technology such as 3.3V logic, 1.0V logic, 0.4V logic, etc. technologies. Moreover, while the examples show input and output as a strictly digital signal, the present circuit may work for other non-digital signals such as a distorted-digital signal, a sine wave signal, a triangle wave signal, etc. to the extent that most digital circuits tolerate.

While FIG. 18 depicts a PSGC that is able to generate up to 127 pulses, a larger number of pulses can be generated if a larger size binary counter and a larger size binary number comparator are used. For example, if the 8-bit binary counter is replaced with a 10-bit binary counter and the 7-bit binary comparator is replaced with a 9-bit binary comparator, the pulse generator can generate up to 511 pulses.

Figure 19:
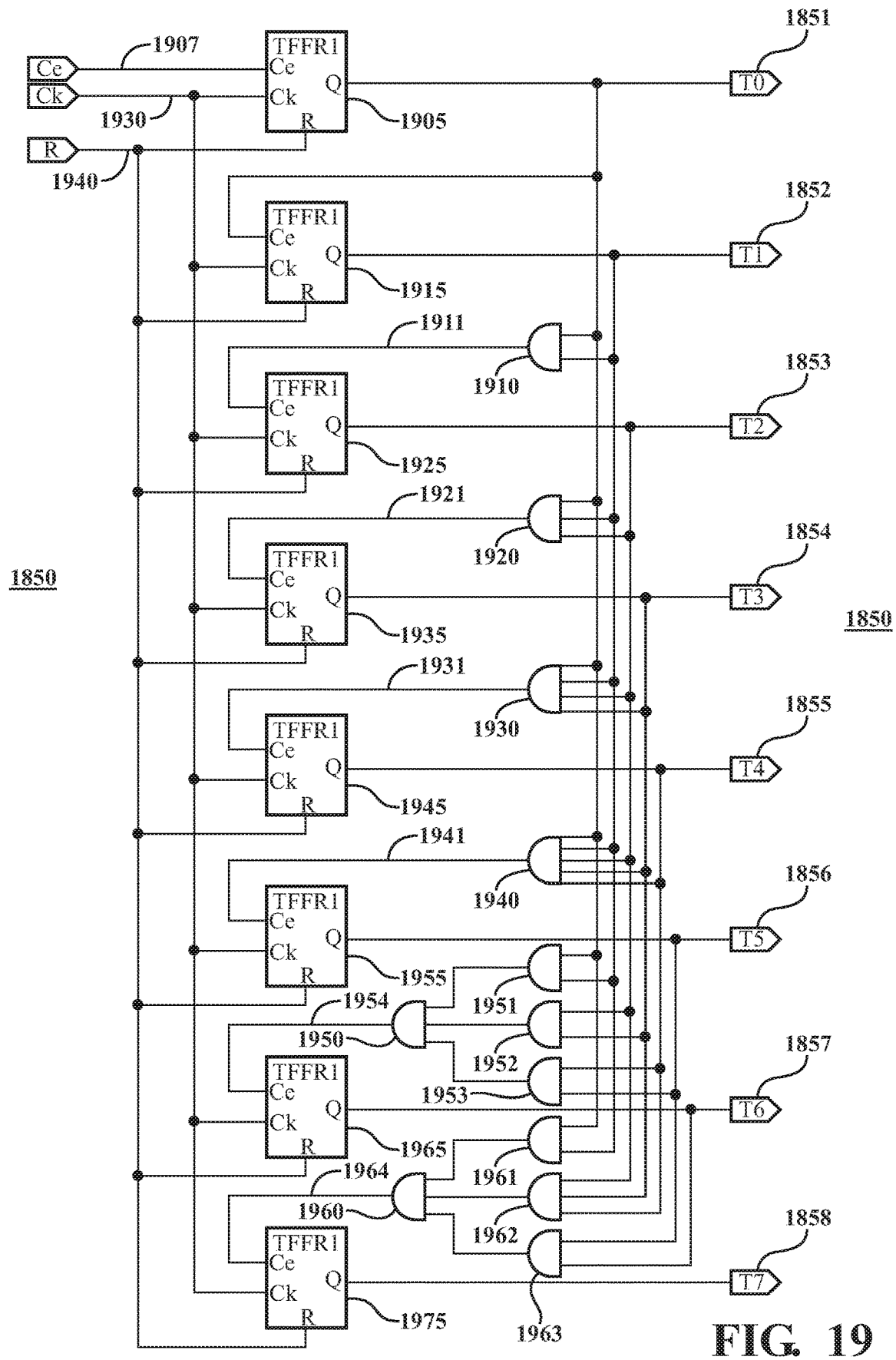
FIG. 19 shows a circuit diagram of an example 8-bit binary counter.

FIG. 19 shows the 8-bit binary counter circuit that may be used in embodiments of the PSGC disclosed in the present disclosure, for example, in the PSGC 1700 shown in FIGS. 17 and 18. The 8-bit binary counter circuit 1850 consists of eight Toggle flip-flop (T-FF) circuits (1905, 1915, 1925, 1935, 1945, 1955, 1965, 1975) and 12 AND gates (1910, 1920, 1930, 1940, 1950, 1951, 1952, 1953, 1960, 1961, 1962, 1963).

Each of the T-FF circuits (1905, 1915, 1925, 1935, 1945, 1955, 1965, 1975) takes clock enable signal "Ce" 1907, input clock signal "Ck" 1930, reset signal "R" 1940 and generates output signal "Q". Clock signal 1930 and reset signal 1940, respectively, provide input clock signal "Ck" and reset signal "R" for all the eight T-FF circuits (1905, 1915, 1925, 1935, 1945, 1955, 1965, 1975).

Enable signal 1907 provides clock enable signal "Ce" for the T-FF 1905. When the enable signal 1907 is high, the T-FF 1905 generates an output signal To 1851. The output signal To 1851 is provided as an input to the clock enable signal "Ce" of T-FF 1915 and the AND gates 1910, 1920, 1930, 1940, 1951, and 1961. Once T-FF 1915 is enabled, T-FF 1915 generates an output signal T1 1852. The output signal T1 1852 is provided as an input to the AND gates 1910, 1920, 1930, 1940, 1951, and 1961. The output 1911 of the AND gate 1910 is provided as an input to the clock enable signal "Ce" of T-FF 1925. Once T-FF 1925 is enabled, T-FF 1925 generates an output signal T2 1853. The output signal T2 1853 is provided as an input to the AND gates 1920, 1930, 1940, 1952, and 1962. The output 1921 of the AND gate 1920 is provided as an input to the clock enable signal "Ce" of T-FF 1935. Once T-FF 1935 is enabled, T-FF 1935 generates an output signal T3 1854. The output signal T3 1854 is provided as an input to the AND gates 1930, 1940, 1952, and 1962. The output 1931 of the AND gate 1930 is provided as an input to the clock enable signal "Ce" of T-FF 1945. Once T-FF 1945 is enabled, T-FF 1945 generates an output signal T4 1855. The output signal T4 1855 is provided as an input to the AND gates 1940, 1953, and 1962. The output 1941 of the AND gate 1940 is provided as an input to the clock enable signal "Ce" of T-FF 1955. Once T-FF 1955 is enabled, T-FF 1955 generates an output signal T5 1856. The output signal T5 1856 is provided as an input to the AND gates 1953, and 1963. The output 1954 of the AND gate 1950 is provided as an input to the clock enable signal "Ce" of T-FF 1965. Once T-FF 1965 is enabled, T-FF 1965 generates an output signal T6 1857. The output signal T6 1857 is provided as an input to the AND gate 1963. The outputs of the AND gates 1961, 1962, 1963 are provided as an input to the AND gate 1960. The output 1964 of the AND gate 1960 is provided as an input to the clock enable signal "Ce" of T-FF 1975. Once T-FF 1975 is enabled, T-FF 1975 generates an output signal T7 1858.

Figure 20:
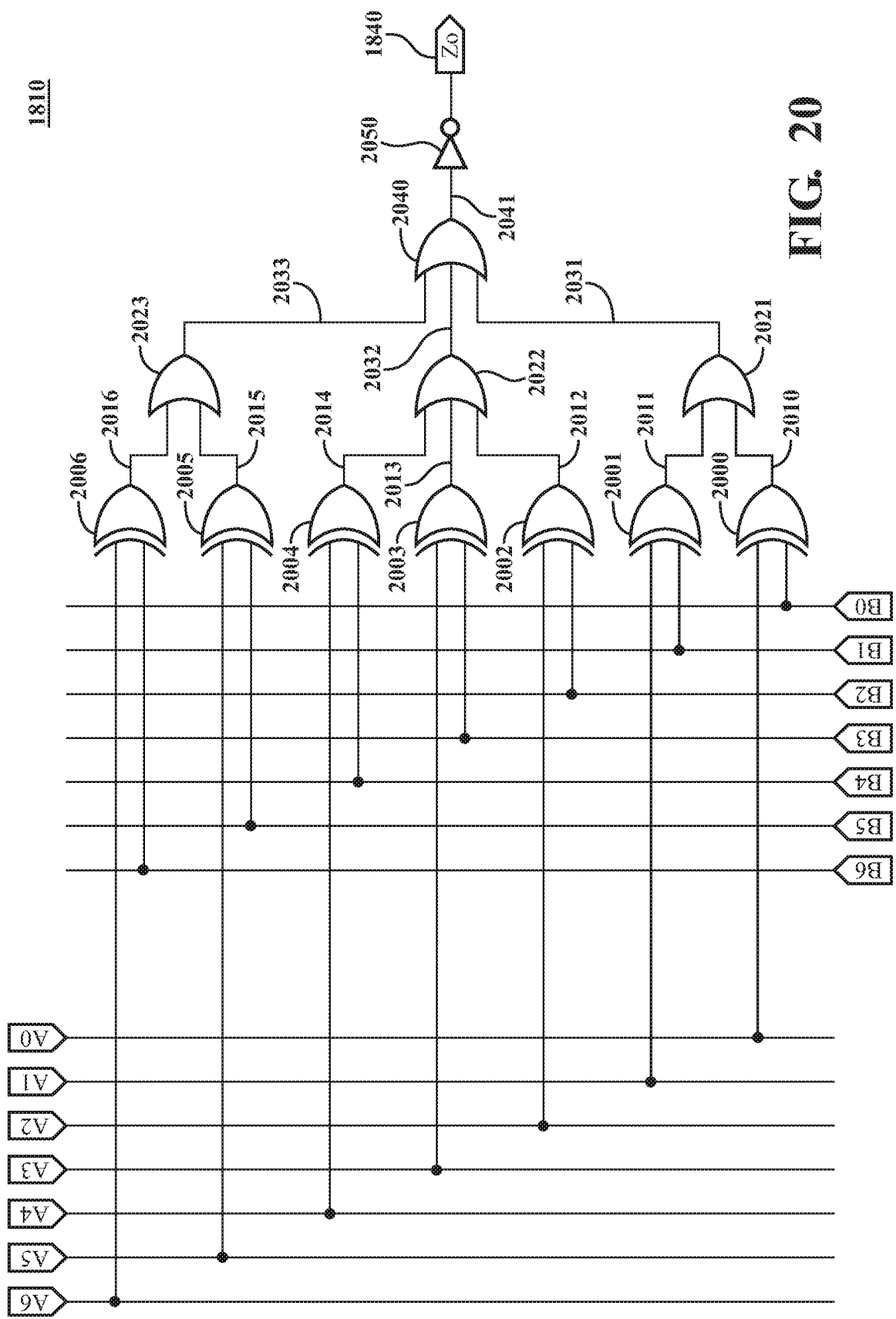
FIG. 20 shows a circuit diagram of an example 7-bit comparator.

FIG. 20 depicts the internal structure of the 7-bit binary comparator circuit 1810. The binary comparator input consists of two binary numbers A and B. The comparator input A consists of the signals A6 through A0, together representing a 7-bit binary number. As a binary number, the signal A6 is the MSB and A0 is the LSB. The comparator input B consists of the signals B6 through B0, together representing a 7-bit binary number. As a binary number, the signal B6 is the MSB and B0 is the LSB. The signals A0 through A6 correspond to the signals A0 through A6 in FIG. 18 which corresponds to the input signals 1861, 1862, 1863, 1864, 1865, 1866, and 1867, respectively. The signal A6 is the MSB and A0 is the LSB. The signals B0 through B6 correspond to B0 through B6 in FIG. 18 which correspond to input signals n0 1730, n1 1731, n2 1732, n3 1733, n4 1734, n5 1735, and n6 1736, respectively. The signal B6 is the MSB and the signal B0 is the LSB.

An XOR gate 2000 receives the signals A0 and B0 as inputs and outputs a signal 2010. An XOR gate 2001 receives the signals A1 and B1 as inputs and outputs a signal 2011. An XOR gate 2002 receives the signals A2 and B2 as inputs and outputs a signal 2012. An XOR gate 2003 receives the signals A3 and B3 as inputs and outputs a signal 2013. An XOR gate 2004 receives the signals A4 and B4 as inputs and outputs a signal 2014. An XOR gate 2005 receives the signals A5 and B5 as inputs and outputs a signal 2015. An XOR gate 2006 receives the signals A6 and B6 as inputs and outputs a signal 2016. An OR gate 2021 receives the signals 2010 and 2011 as inputs and outputs a signal 2031. An OR gate 2022 receives the signals 2012, 2013 and 2014 as inputs and outputs a signal 2032. An OR gate 2023 receives the signals 2015 and 2016 as inputs and outputs a signal 2033. An OR gate 2040 receives the signals 2031, 2032, and 2033 as inputs and outputs a signal 2041. An inverter 2050 inverts the signal 2041 and outputs a signal Zo 1840.

The output signal Zo of 7-bit binary comparator circuit 1810 becomes logic high if the binary number A0 through A6 and the binary number B0 through B6 are equal. If the binary number A0 through A6 and the binary number B0 through B6 are not equal, the output signal Zo of 7-bit binary comparator circuit 1810 becomes logic low. For example, when the binary number B0 through B6 is 000011 and the binary number A0 through A6 is 000011, the output signal Zo becomes logic high. In contrast, when the binary number B0 through B6 is 000011 and the binary number A0 through A6 is 000010, then the output signal Zo becomes logic low. The present pulse sequence generator circuit such as the pulse sequence generator circuit 1700 may be adopted in a very small hand-held high-frequency ultrasound scanner that requires a small battery to operate.

Figure 23:
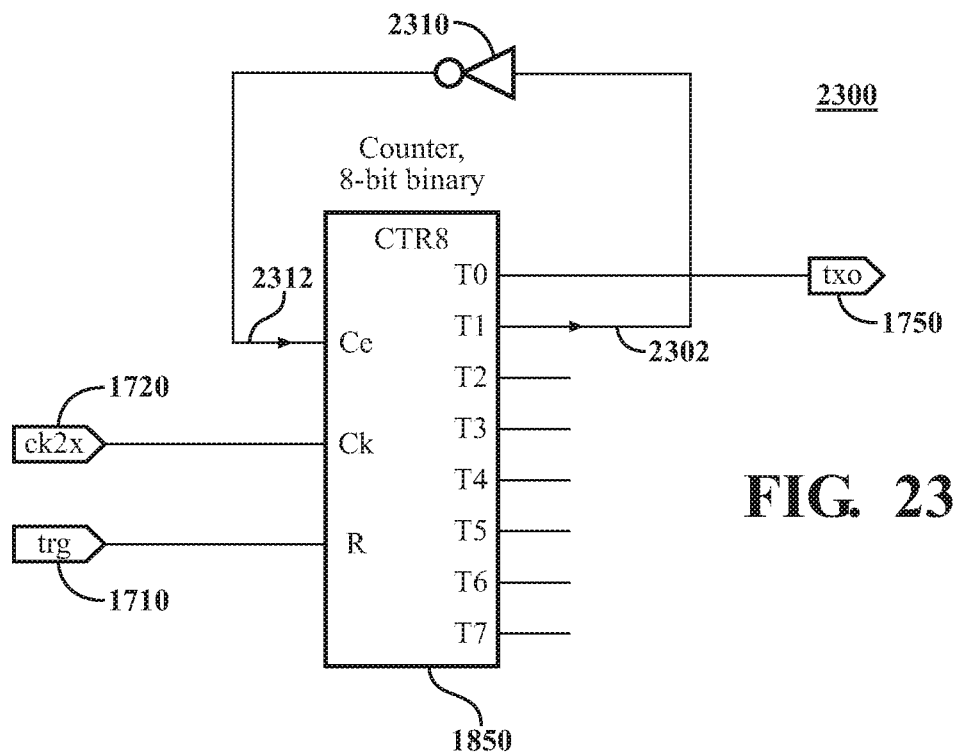
FIG. 23 shows a simplified PSGC that generates a single pulse.

While the PSGC 1700 in FIG. 18 includes the counter 1850 and the comparator 1810, a simplified pulse sequence generator circuit without a comparator may be implemented. FIG. 23 illustrates a simplified PSGC 2300, according to another embodiment shown and described herewith. The PSGC 2300 includes an 8-bit binary counter 1850 without a comparator. The PSGC 2300 receives the trigger signal 1710 and the clock signal 1720 and outputs a pulse sequence output Txo 1750. As illustrated in FIG. 23, instead of providing output signals T1 through T7 to a comparator, only the output signal T1 2302 is inverted via an inverter 2310, and the inverted signal 2312 is provided to the 8-bit binary counter circuit 1850 as a clock enable signal "Ce." Accordingly, the PSGC 2300 operates as a signal pulse generator by outputting a single pulse through the pulse sequence output Txo 1750.

Figure 24:
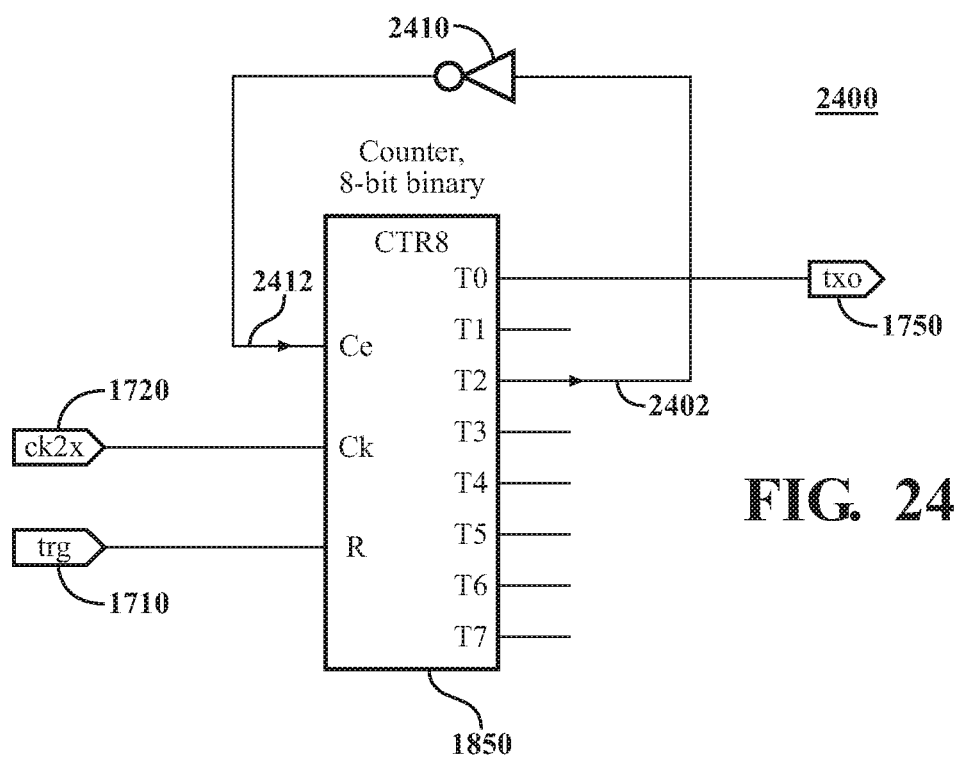
FIG. 24 shows a simplified PSGC that generates two pulses.

FIG. 24 illustrates a simplified PSGC 2400, according to another embodiment shown and described herewith. The PSGC 2400 includes an 8-bit binary counter 1850 without a comparator. The PSGC 2400 receives the trigger signal 1710 and the clock signal 1720 and outputs a pulse sequence output Txo 1750. As illustrated in FIG. 24, instead of providing output signals T1 through T7 to a comparator, only the output signal T2 2402 is inverted via an inverter 2410, and the inverted signal 2412 is provided to the 8-bit binary counter circuit 1850 as a clock enable signal "Ce." Accordingly, the PSGC 2400 operates as a two pulse generator by outputting two pulses through the pulse sequence output To 1750.

Figure 25:
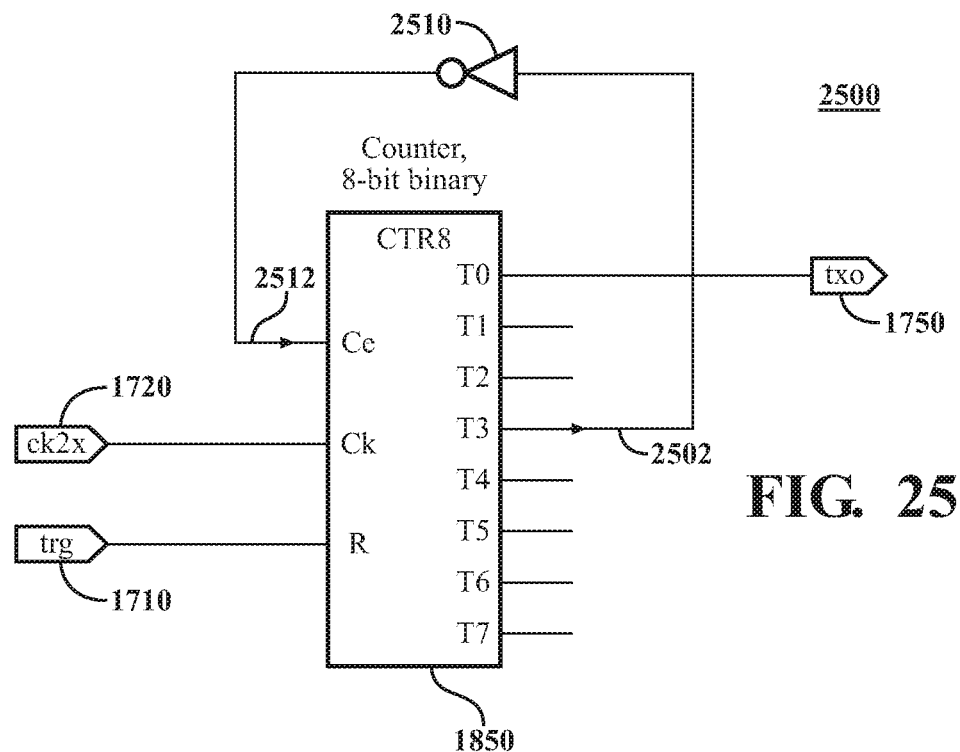
FIG. 25 shows a simplified PSGC that generates four pulses.

FIG. 25 illustrates a simplified PSGC 2500, according to another embodiment shown and described herewith. The PSGC 2500 includes an 8-bit binary counter 1850 without a comparator. The PSGC 2500 receives the trigger signal 1710 and the clock signal 1720 and outputs a pulse sequence output Txo 1750. As illustrated in FIG. 25, instead of providing output signals T1 through T7 to a comparator, only the output signal T3 2502 is inverted via an inverter 2510, and the inverted signal 2512 is provided to the 8-bit binary counter circuit 1850 as a clock enable signal "Ce." Accordingly, the PSGC 2500 operates as a four pulse generator by outputting four pulses through the pulse sequence output Txo 1750.

Figure 26:
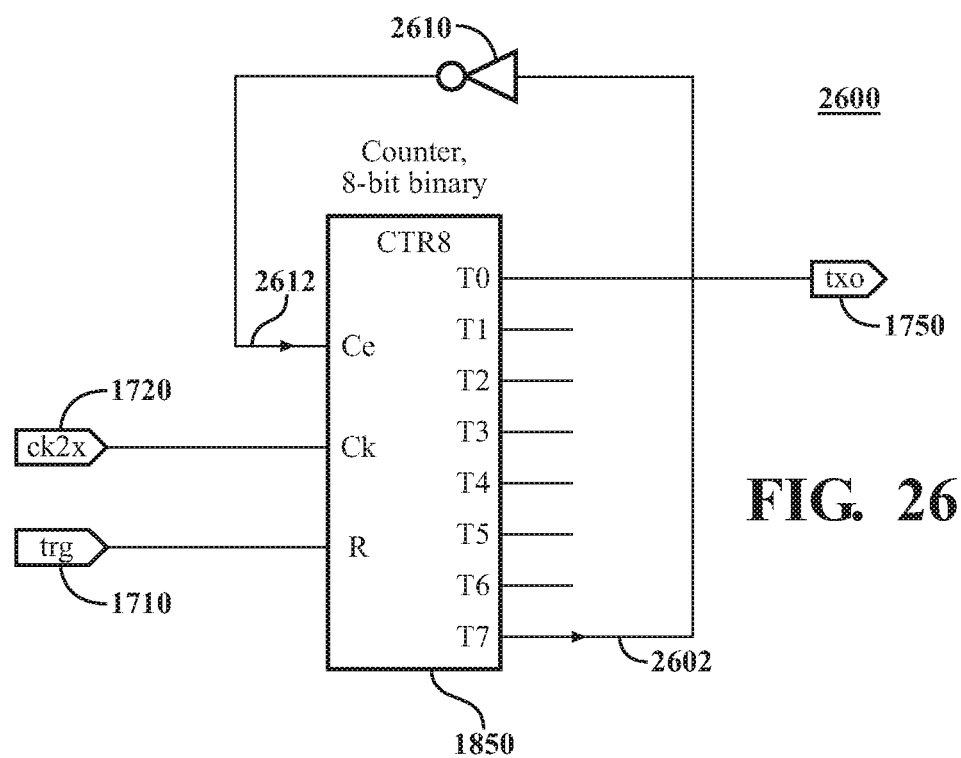
FIG. 26 shows a simplified PSGC that generates sixty-four pulses.

FIG. 26 illustrates a simplified PSGC 2600, according to another embodiment shown and described herewith. The PSGC 2600 includes an 8-bit binary counter 1850 without a comparator. The PSGC 2300 receives the trigger signal 1710 and the clock signal 1720 and outputs a pulse sequence output Txo 1750. As illustrated in FIG. 26, instead of providing output signals T1 through T7 to a comparator, only the output signal T7 2602 is inverted via an inverter 2610, and the inverted signal 2612 is provided to the 8-bit binary counter circuit 1850 as a clock enable signal "Ce." Accordingly, the PSGC 2600 operates as a sixty-four pulse generator by outputting sixty-four pulses through the pulse sequence output Txo 1750.

While not illustrated in figures, if the output signal T4 of the counter 1850 is inverted and provided to the counter 1850 as a clock enable signal, the PSGC operates as an eight pulse generator. Similarly, if the output signal T5 of the counter 1850 is inverted and provided to the counter 1850 as a clock enable signal, the PSGC operates as a sixteen pulse generator. If the output signal T6 of the counter 1850 is inverted and provided to the counter 1850 as a clock enable signal, the PSGC operates as a thirty-two pulse generator.

Figure 27:
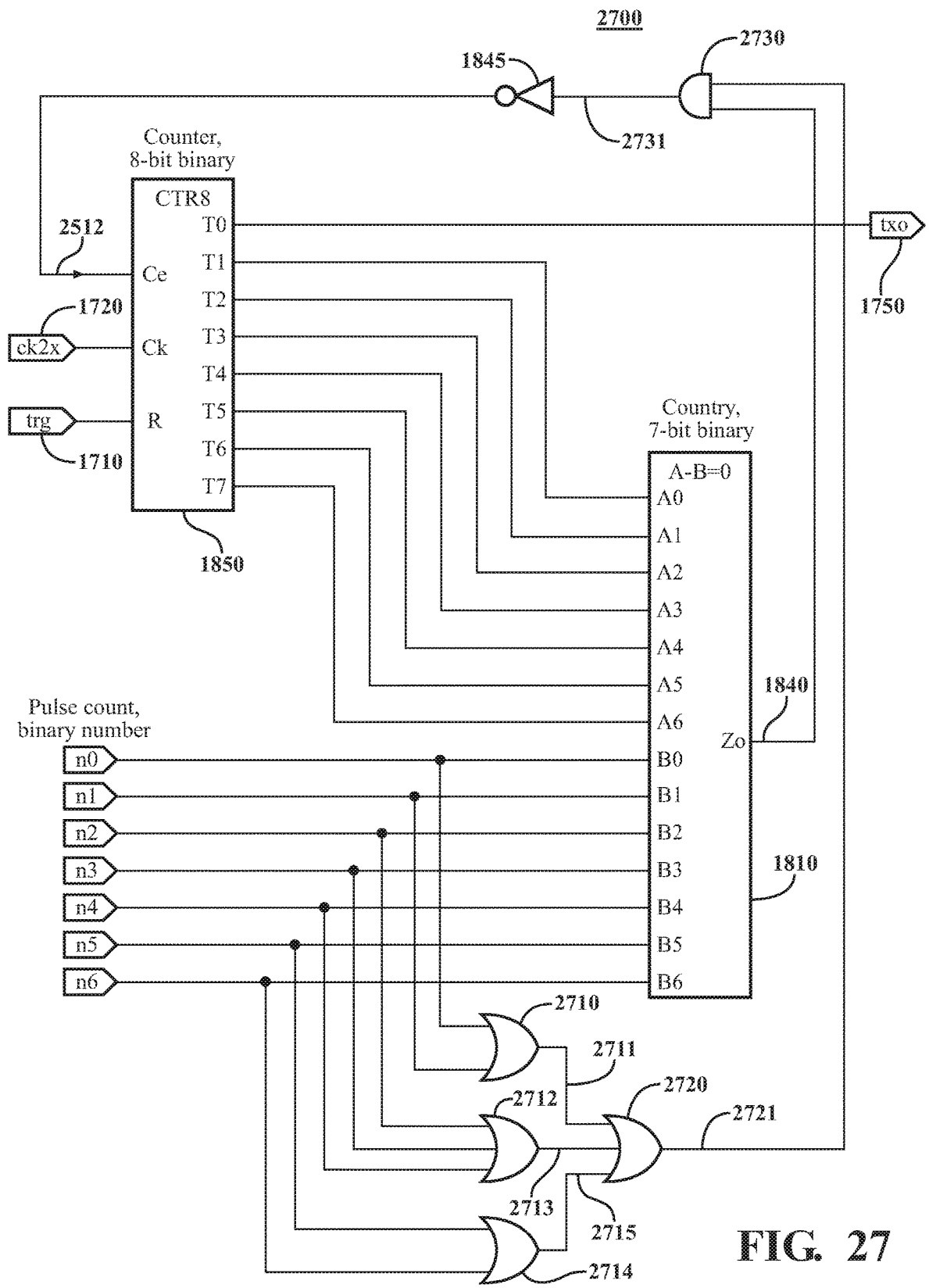
FIG. 27 shows a circuit diagram of another embodiment of the PSGC.

FIG. 27 depicts a variation of the PSGC, according to another embodiment shown and described herewith. The PSGC 2700 includes the 8-bit binary counter circuit 1850 and the 7-bit binary comparator circuit 1810 similar to the PSGC 1700 in FIG. 18. Additionally, the PSGC 2700 includes four OR gates 2710, 2712, 2714, 2720 and one AND gate 2730. The OR gate 2710 receives n0 and n1 signals as inputs and outputs a signal 2711. The OR gate 2712 receives n2, n3 and n4 signals as inputs and outputs a signal 2713. The OR gate 2714 receives n5 and n6 as inputs and outputs a signal 2715. The OR gate 2720 receives signals 2711, 2713, and 2715 as inputs and outputs a signal 2721. The AND gate 2730 receives the output signal 1840 and the signal 2721 as inputs, and outputs a signal 2731. The signal 2731 is inverted through the inverter 1845 and the inverted signal is provided to the 8-bit binary counter 1850 as a clock enable signal.

The PSGC 2700 generates the same number of pulses as the PSGC 1700 in FIGS. 17 and 18. However, when the pulse count number n is set to 0 (i.e., n0=0, n1=0, n2=0, n3=0, n4=0, n5=0, n6=0), a continuous pulse output is generated at the pulse sequence output 1750. That is, a continuous pulse may be generated with additional few gates being added to the PSGC 1700.

In some embodiments, the zero-detector circuit including the four OR gates 2710, 2712, 2714, 2720 may be replaced with a single 7-input OR gate. The four OR gates 2710, 2712, 2714, 2720 and the single 7-input OR gate are logically equivalent, and they are essentially the same circuit. The zero-detector circuit with four OR gates may be more suitable for the implementation with discrete circuit components and the single 7-input OR gate implementation of the zero-detector circuit may be more suitable for an integrated circuit technology.

Various PSGCs are described herein. However, it should be understood that this is merely illustrative, and other arrangements of the ultrasound imaging system and transmit signal generator relative to the above discussed various components thereof are contemplated and included within the scope of the present disclosure. Specifically, logically equivalent circuits may be employed. For example, NAND-NOR circuit implementation which is logically equivalent of AND-OR-NOT circuit implementation may be employed. In addition, when the described pulse sequence generator circuit is optimized by a computer program or by a person, the resulting logically equivalent circuit is effectively the same as the pulse sequence generator circuit described in the present disclosure. Most of the FPGA synthesis and implementation programs run the automatic optimization before finalizing the circuit configuration, and the resulting circuit is the same as the initial circuit, i.e., logically equivalent.

Another example of the logically equivalent circuits are the CMOS chip technology with different logic styles. There are pass-transistor logic, dynamic logic, ratioed pseudo NMOS logic, full static complimentary CMOS logic, etc. for implementing a digital circuit of a logic function. That is, same logic function can be implemented in different logic style because they are logically and functionally equivalent. The pulse sequence generator circuit described in this patent application can be implemented with various different logic styles in the CMOS chip technology. I do claim the logically equivalent circuit as same circuit, for the pulse generator circuit described in this application, implemented in different logic style in the CMOS chip technology.

The foregoing detailed description has been presented for purposes of illustration and description. It is not intended to be exhaustive or to limit embodiments to the precise form disclosed. Many modifications and variations are possible in light of the above teaching. The described embodiments were chosen in order to explain principles and practical applications, to thereby enable others skilled in the art to best utilize various embodiments and with various modifications as are suited to the particular use contemplated. It is intended that the scope be defined by the claims appended hereto.

What is claimed is:

1. A transmit signal generator for generating a sequence of pulses, comprising:
   an n−1 bit comparator having a first set of n−1 input lines and a second set of n−1 input lines and an output line providing an output of the n−1 bit comparator, the n−1 bit comparator operable to compare signals of the first set of n−1 input lines and signals of the second set of n−1 input lines and provide the output of the n−1 bit comparator based on the comparison; and
   an n-bit binary counter having a clock signal input line connected to a clock signal input, a reset signal input line connected to a reset signal input, a clock enable line connected to the output line of the n−1 bit comparator providing the output of the n−1 bit comparator as an input signal for the clock enable line, and n output lines, one of the n output lines providing a sequence of pulse as an output of the transmit signal generator and the remaining of the n output lines of the n-bit binary counter each connected to one of the second set of n−1 input lines of the n−1 bit comparator,
   wherein the output of the transmit signal generator provides a continuous pulse or an N pulse sequence as the output based on the signals of the second set of n−1 input lines and the reset signal input initiating generation of the sequence of pulses, wherein $N \le 2^{n-1}-1$ and n is an integer.

2. The transmit signal generator of claim 1, further comprising an inverter between the output line of the n−1 bit comparator and the clock enable line for inverting the output of the n−1 bit comparator and providing the inverted output as the input signal for the clock enable line of the n-bit binary counter.

3. The transmit signal generator of claim 1, further comprising:
   one or more OR gates receiving the signals of the second set of n−1 input lines as inputs and outputting an OR output;
   an AND gate receiving the output of the n−1 bit comparator and the OR output of the one or more OR gates as inputs and outputting an AND output; and
   an inverter for inverting the AND output and providing the inverted output as the input signal for the clock enable line of the n-bit binary counter.

4. The transmit signal generator of claim 1, wherein the one of the n output lines providing the sequence of pulses as the output is a least significant bit of the n output lines of the n-bit binary counter.

5. The transmit signal generator of claim 1, wherein the clock signal input for the n-bit binary counter has a frequency of H Hz and the output of the transmit signal generator has a frequency of H/2 Hz.

6. The transmit signal generator of claim 1, wherein the n-bit binary counter is a n-bit frequency counter comprising n Toggle flip-flop (T-FF) circuits and a plurality of AND gates.

7. The transmit signal generator of claim 6, wherein at least one of the T-FF circuits comprises a Data flip-flop (D-FF) circuit and an inverter.

8. The transmit signal generator of claim 6, wherein at least one of the T-FF circuits comprises a Data flip-flop (D-FF), two inverters, two AND gates and an OR gate.

9. An ultrasound imaging system, comprising the transmit signal generator of claim 1.

10. A transmit signal generator for generating a sequence of pulses, comprising:
    a n-bit binary counter having a clock signal input line connected to a clock signal input, a reset signal input line connected to a reset signal input, a clock enable line, and n output lines,
    wherein:
    one of the n output lines provides a sequence of pulse as an output of the transmit signal generator, and the clock enable line is connected to one of the remaining of the n output lines of the n-bit binary counter, and
    the output of the transmit signal generator provides a L pulse sequence as the output based on which one of the remaining of the n output lines of the n-bit binary counter is connected to the clock enable line, wherein L is $2^{m-2}$, $m \le n$, and m and n are an integer.

11. The transmit signal generator of claim 10, further comprising an inverter between the one of the remaining of the n output lines of the n-bit binary counter and the clock enable line for inverting the output of the one of the remaining of the n output lines of the n-bit binary counter and providing the inverted output as an input signal for the clock enable line of the n-bit binary counter.

12. The transmit signal generator of claim 10, wherein the one of the n output lines providing the sequence of pulses as the output is a least significant bit of the n output lines of the n-bit binary counter.

13. The transmit signal generator of claim 10, wherein the clock signal input for the n-bit binary counter has a frequency of H Hz and the output of the transmit signal generator has a frequency of H/2 Hz.

14. The transmit signal generator of claim 10, wherein the n-bit binary counter is a n-bit frequency counter comprising n Toggle flip-flop (T-FF) circuits and a plurality of AND gates.

15. The transmit signal generator of claim 14, wherein at least one of the T-FF circuits comprises a Data flip-flop (D-FF), two inverters, two AND gates and an OR gate.

16. An ultrasound imaging system, comprising the transmit signal generator of claim 14.

17. A transmit signal generator for generating a sequence of pulses, comprising:
    a $2^n$-to-1 multiplexer having $2^n$ input lines, one of the $2^n$ input lines being connected to a clock signal input, n selector lines connected to a selector signal and an output line providing an output of the $2^n$-to-1 multiplexer, the $2^n$-to-1 multiplexer operable to select one of the $2^n$ input lines as the output of the $2^n$-to-1 multiplexer based on the selector signal; and
    a $2^n$-bit binary counter having a clock signal input line connected to the clock signal input, a reset signal input line connected to a reset signal input, a clock enable line connected to the output line of the $2^n$-to-1 multiplexer providing the output of the $2^n$-to-1 multiplexer as an input signal for the clock enable line, and $2^n$ output lines, one of the $2^n$ output lines providing a sequence of pulse as an output of the transmit signal generator and the remaining $2^n$ output lines of the $2^n$-bit binary counter each connected to one of the remaining $2^n$ input lines of the $2^n$-to-1 multiplexer;
    wherein the output of the transmit signal generator provides a continuous pulse or an N pulse sequence as the output based on the selector signal and the reset signal input initiating generation of the sequence of pulses, wherein $N \le 2^n$ and n is an integer.

18. The transmit signal generator of claim 17, further comprising:
  at least one ($2^n-2$) integer-number detector circuit;
  each of the remaining $2^n$ output lines of the $2^n$-bit binary counter connected to each of the at least one integer-number detector circuit as input; and
  each of the at least one integer-number detector circuit having an output line connected to one of the remaining $2^n$ input lines of the $2^n$-to-1 multiplexer, wherein N is a positive integer number.

19. The transmit signal generator of claim 18, wherein each of the at least one integer-number detector circuit comprise an AND gate and one or more inverters.

20. An ultrasound imaging system, comprising the transmit signal generator of claim 17.

* * * * *